United States Patent
Seifert et al.

(10) Patent No.: US 10,449,093 B2
(45) Date of Patent: Oct. 22, 2019

(54) FINGERTIP CLEANING APPARATUS

(71) Applicant: FINGERTIPS ENTERPRISES, LLC, New York, NY (US)

(72) Inventors: Alon Seifert, New York, NY (US); Eitan Cohen, New York, NY (US); Matthew L. Chin, New York, NY (US); Gareth Brown, Jersey City, NJ (US); Stephen Kaes, New York, NY (US)

(73) Assignee: FINGERTIPS ENTERPRISE, LLC, New York, NY (US)

(*) Notice: Subject to any disclaimer, the term of this patent is extended or adjusted under 35 U.S.C. 154(b) by 81 days.

(21) Appl. No.: 15/494,084

(22) Filed: Apr. 21, 2017

(65) Prior Publication Data
US 2017/0304120 A1 Oct. 26, 2017

Related U.S. Application Data

(60) Provisional application No. 62/325,600, filed on Apr. 21, 2016.

(51) Int. Cl.
*A61F 11/00* (2006.01)
*B65D 85/62* (2006.01)
*A47K 7/02* (2006.01)

(52) U.S. Cl.
CPC .............. *A61F 11/006* (2013.01); *A47K 7/02* (2013.01); *B65D 85/62* (2013.01)

(58) Field of Classification Search
CPC ......... A61F 11/006; A47K 7/02; B65D 85/62; A46B 5/04
See application file for complete search history.

(56) References Cited

U.S. PATENT DOCUMENTS 2,016,951 A * 10/1935 Welker .................... A46B 5/04
15/227
2,075,681 A * 3/1937 Welker .................... A46B 5/04
15/188
2,092,987 A * 9/1937 Remington .............. A46B 5/04
15/227

(Continued)

FOREIGN PATENT DOCUMENTS

GB 2324241 10/1998
WO 03043528 5/2003
(Continued)

OTHER PUBLICATIONS

Corresponding International Search Report and Written Opinion for PCT/US2017/028888 dated Aug. 14, 2017.

*Primary Examiner* — Shaun L David
*Assistant Examiner* — Brigid K Byrd
(74) *Attorney, Agent, or Firm* — The Belles Group, P.C.

(57) ABSTRACT

Described herein is a fingertip cleaning apparatus comprising a fingertip receiving portion including a conical wall defining a cavity having an open end configured to allow a fingertip of a user to be inserted into the cavity, the conical wall extending along and surrounding a cone axis, the conical wall forming a cone angle with the cone axis, a gripping portion comprising a flap that extends from the conical wall of the e fingertip receiving portion along a grip axis that forms a grip angle with the cone axis; and the grip angle being greater than the once angle.

20 Claims, 26 Drawing Sheets

(56) References Cited

U.S. PATENT DOCUMENTS

| | | | | |
|---|---|---|---|---|
| 2,101,363 A * | 12/1937 | De Rome | A46B 5/04 | 15/227 |
| 2,439,056 A * | 4/1948 | Rathbun | A46B 5/04 | 15/104.94 |
| 2,686,325 A * | 8/1954 | Silver | A46B 1/00 | 15/188 |
| 2,966,691 A * | 1/1961 | Cameron | A46B 5/04 | 128/846 |
| 3,018,498 A * | 1/1962 | Wasserman | A46B 5/04 | 15/167.1 |
| 3,124,824 A * | 3/1964 | Lutz | A61C 17/00 | 15/104.94 |
| 3,348,541 A * | 10/1967 | Loebeck | A61F 13/105 | 2/21 |
| 3,675,264 A * | 7/1972 | Storandt | A46B 5/04 | 15/104.94 |
| 3,902,509 A * | 9/1975 | Tundermann | A61C 15/02 | 433/142 |
| 3,905,113 A * | 9/1975 | Jacob | A46B 5/04 | 15/167.1 |
| 3,934,299 A * | 1/1976 | Regester | A46B 5/04 | 15/104.94 |
| 3,984,148 A * | 10/1976 | Regester | A46B 5/04 | 300/21 |
| 4,177,811 A | 12/1979 | Alvarez | | |
| 4,251,897 A * | 2/1981 | Alam | A46B 5/00 | 15/167.1 |
| 4,335,731 A * | 6/1982 | Bora, Jr. | A46B 11/0003 | 15/104.93 |
| 4,620,528 A * | 11/1986 | Arraval | A46B 5/04 | 15/167.1 |
| 5,045,073 A | 9/1991 | Wagner | | |
| 5,107,562 A * | 4/1992 | Dunn | A46B 5/04 | 15/167.1 |
| 5,213,428 A * | 5/1993 | Salman | A46B 5/04 | 15/167.1 |
| 5,348,153 A * | 9/1994 | Cole | A46B 5/04 | 15/167.1 |
| 5,440,774 A * | 8/1995 | Cole | A46B 5/04 | 15/105 |
| 5,487,201 A * | 1/1996 | Hansen | A46B 5/04 | 132/309 |
| 5,502,863 A * | 4/1996 | Perkins | A46B 5/04 | 15/118 |
| 5,604,952 A | 2/1997 | Zeleznick | | |
| 5,609,165 A | 3/1997 | Lambert | | |
| 5,715,850 A | 2/1998 | Markgraaf | | |
| 5,761,743 A * | 6/1998 | Andrews | A41D 13/087 | 2/161.7 |
| 5,807,301 A * | 9/1998 | Nadam | A61F 11/006 | 15/227 |
| 5,875,513 A * | 3/1999 | Reinold | A46B 5/04 | 15/167.1 |
| 5,954,245 A * | 9/1999 | Kluesner | D05B 91/04 | 2/21 |
| 6,022,140 A | 2/2000 | Fraden et al. | | |
| 6,105,587 A * | 8/2000 | Dunn | A46B 5/04 | 132/309 |
| 6,112,356 A * | 9/2000 | Hashey | A46B 5/04 | 15/104.94 |
| 6,155,987 A | 12/2000 | Scherl | | |
| 6,243,868 B1 * | 6/2001 | Wanzenried | A41D 13/087 | 2/21 |
| 6,336,461 B1 * | 1/2002 | Martinez | A46B 5/04 | 132/309 |
| 6,695,802 B1 | 2/2004 | Thompson | | |
| 6,808,068 B2 * | 10/2004 | Abada | A46B 5/04 | 132/308 |
| 6,874,194 B1 * | 4/2005 | Harris | A46B 5/04 | 15/167.1 |
| 7,056,309 B1 | 6/2006 | Hennigan | | |
| 7,237,949 B2 | 7/2007 | Lantz et al. | | |
| 7,316,034 B1 * | 1/2008 | Berry | A41D 13/087 | 132/73 |
| 7,507,047 B2 * | 3/2009 | Oberstadt | A46B 5/04 | 401/132 |
| 7,517,166 B2 * | 4/2009 | Keck | A45D 34/04 | 401/201 |
| 7,789,845 B1 * | 9/2010 | Meliti | A41D 13/087 | 2/163 |
| 7,959,902 B1 * | 6/2011 | Postlewaite | A46B 5/04 | 132/308 |
| 8,196,746 B2 * | 6/2012 | Storandt | A45C 11/24 | 206/369 |
| 8,261,938 B2 * | 9/2012 | Oradini, Sr. | B65D 83/08 | 221/33 |
| 8,398,323 B2 * | 3/2013 | Kotturan | A46B 5/04 | 401/6 |
| 8,584,684 B2 * | 11/2013 | Nakamura | A45D 31/00 | 132/74.5 |
| 8,662,091 B2 | 3/2014 | Jang | | |
| D710,060 S | 7/2014 | Gurley | | |
| D753,835 S * | 4/2016 | Pettygrove | D24/189 | |
| 9,820,560 B1 * | 11/2017 | Crowley | A46B 5/04 | |
| 2002/0026679 A1 * | 3/2002 | Widlund | A47K 7/02 | 15/227 |
| 2003/0081980 A1 * | 5/2003 | Moga | A47K 7/02 | 401/7 |
| 2005/0142519 A1 * | 6/2005 | Atzori | A46B 5/04 | 433/216 |
| 2006/0143767 A1 * | 7/2006 | Yang | A41D 19/015 | 2/16 |
| 2006/0242780 A1 * | 11/2006 | Yang | A45D 34/04 | 15/227 |
| 2007/0041923 A1 | 2/2007 | Okajima et al. | | |
| 2007/0083980 A1 * | 4/2007 | Yang | A41D 19/0006 | 2/167 |
| 2008/0257757 A1 * | 10/2008 | Storandt | A45C 11/24 | 206/37 |
| 2009/0035048 A1 * | 2/2009 | Safieh | A46B 5/04 | 401/7 |
| 2009/0112241 A1 | 4/2009 | Bar et al. | | |
| 2010/0088794 A1 * | 4/2010 | Oradini, Sr. | A41D 13/087 | 2/21 |
| 2011/0270290 A1 * | 11/2011 | Nadam | A61F 13/38 | 606/162 |
| 2013/0211434 A1 * | 8/2013 | Leach | A61F 11/006 | 606/162 |
| 2014/0007817 A1 * | 1/2014 | Fanelli | A01K 13/001 | 119/603 |
| 2014/0223682 A1 * | 8/2014 | Sabet | A46B 5/04 | 15/167.1 |
| 2015/0351968 A1 * | 12/2015 | Shane | A61F 11/006 | 606/162 |
| 2016/0157594 A1 * | 6/2016 | Jones | A46B 5/04 | 15/160 |
| 2017/0087024 A1 * | 3/2017 | Al-Bakkour | A61F 11/006 | |
| 2017/0304120 A1 * | 10/2017 | Seifert | A47K 7/02 | |

FOREIGN PATENT DOCUMENTS

| | | |
|---|---|---|
| WO | 2009115668 | 9/2009 |
| WO | 2011062838 | 5/2011 |

\* cited by examiner

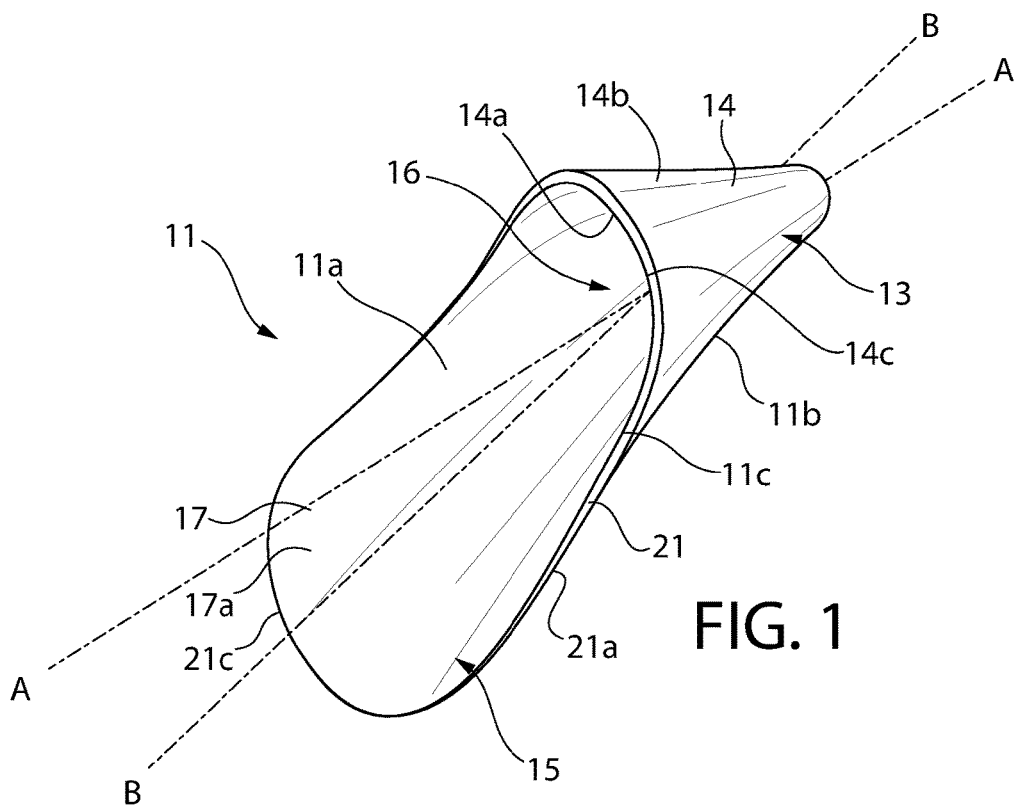
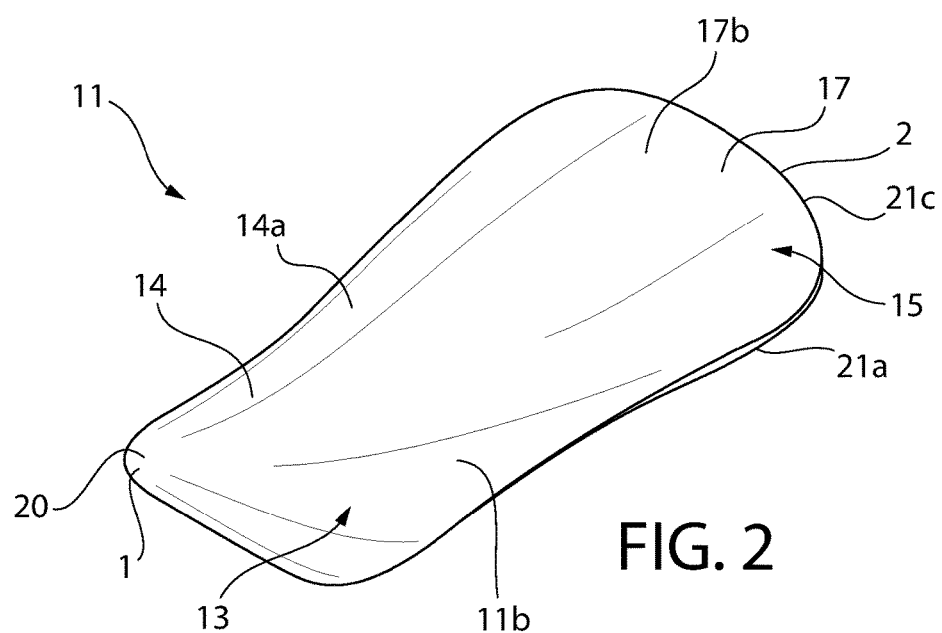

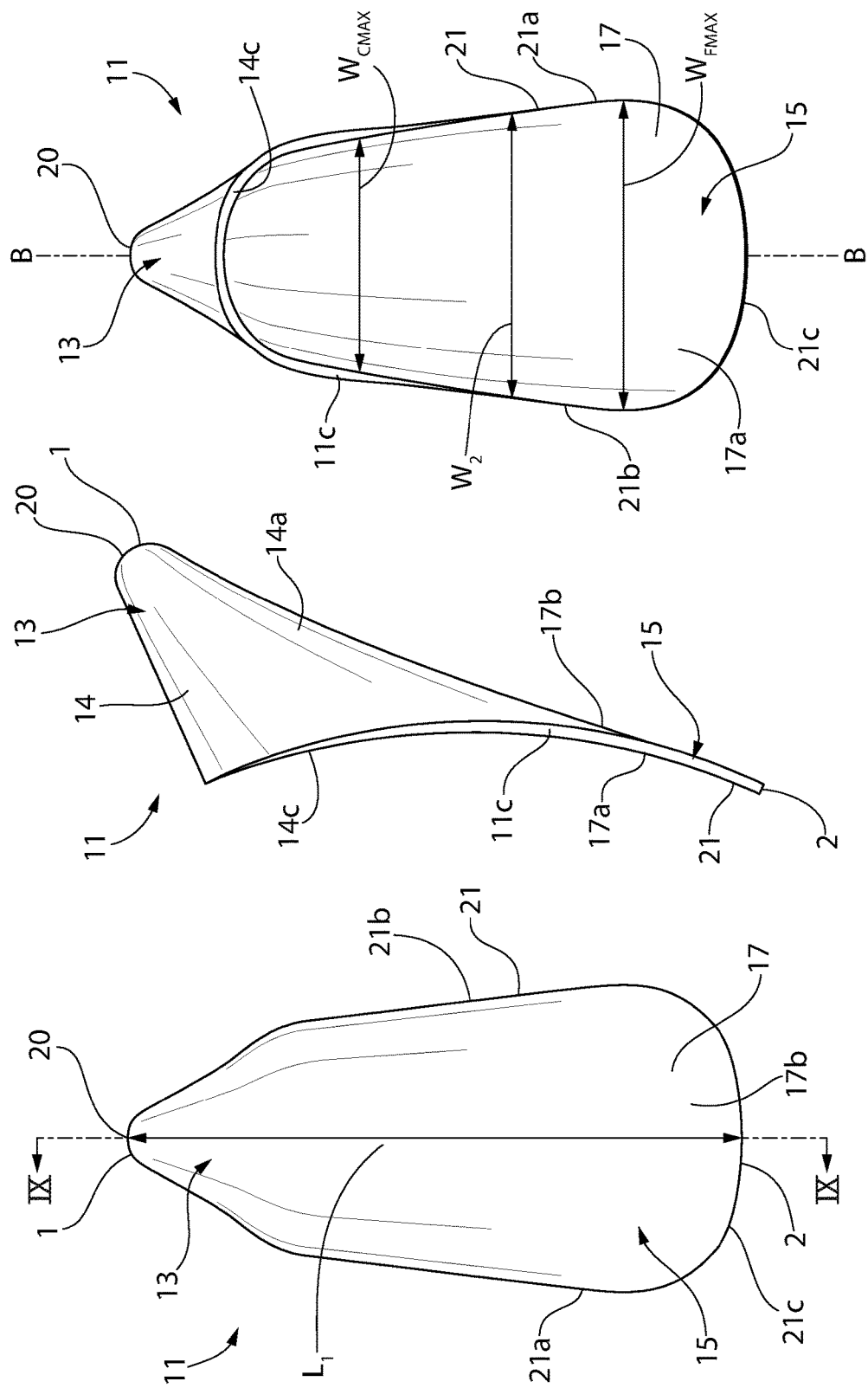

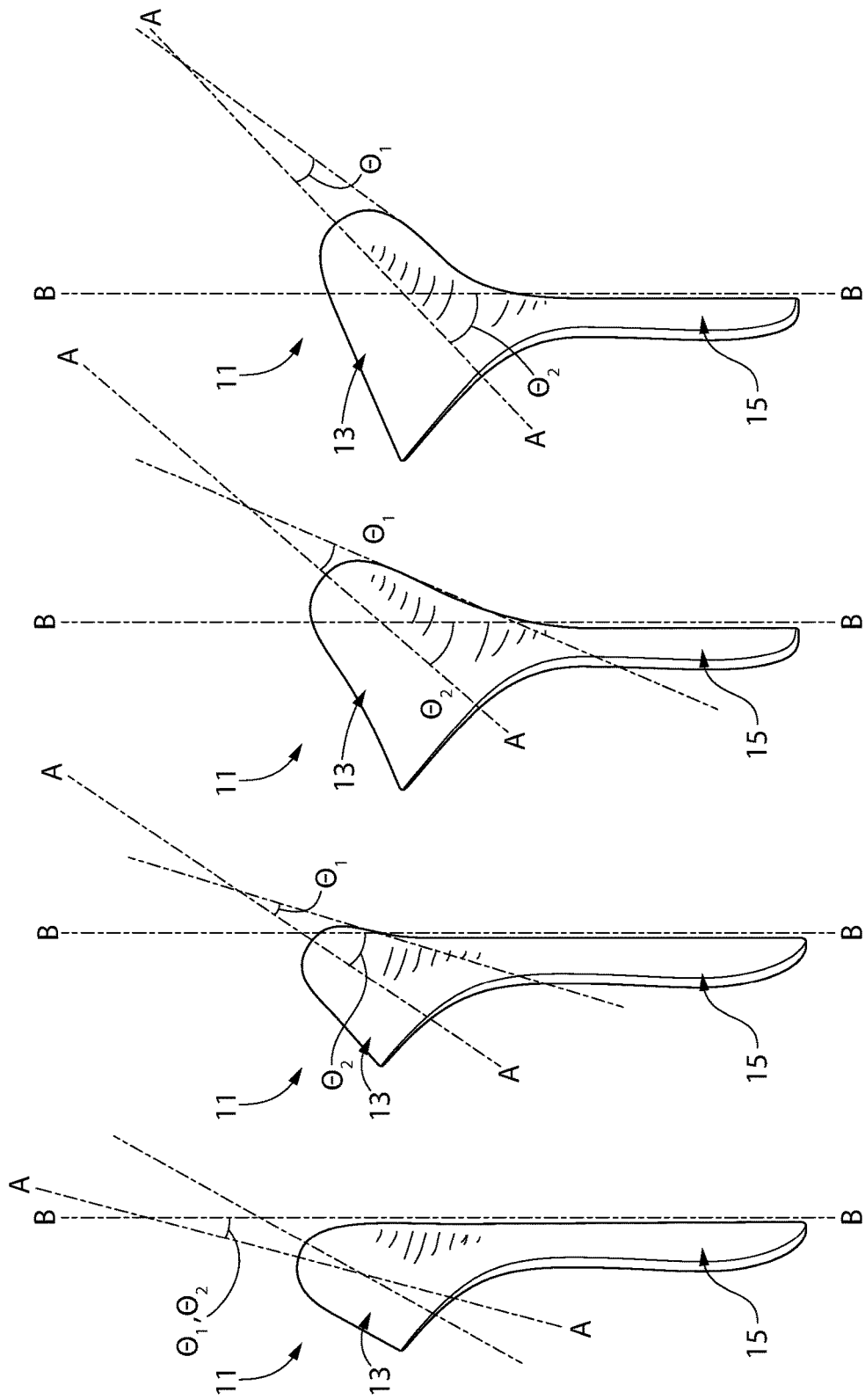

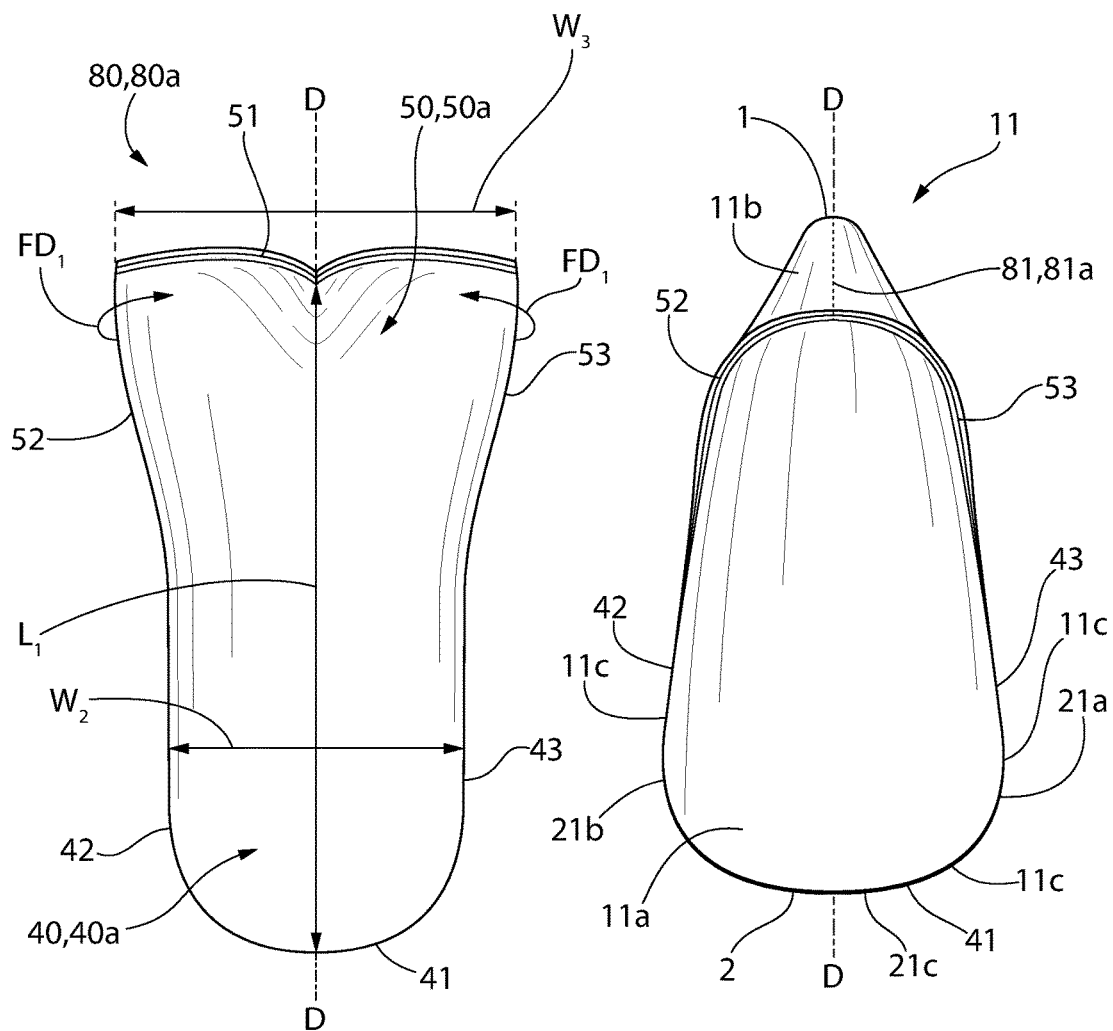

FINGERTIP CLEANING APPARATUS

CROSS-REFERENCE TO RELATED APPLICATIONS

This application claims the benefit of U.S. Provisional Application No. 62/325,600, filed on Apr. 21, 2016. The disclosure of the above application is incorporated herein by reference

FIELD OF THE INVENTION

The field of the present invention relates to cleaning devices placed over the finger for cleaning external body surfaces.

BACKGROUND OF THE INVENTION

Earwax, also known by the medical term cerumen, is a yellowish waxy substance secreted in the ear canal of humans and other mammals. It protects the skin of the human ear canal, assists in cleaning and lubrication, and also provides some protection from bacteria, fungi, insects, and water.

Earwax is good for the overall health of the ear, a fact to which practically every doctor will attest. However, nobody seems to care about what doctors think when it comes to earwax and earwax build-up. Almost everybody cleans their ears for aesthetic reasons, even at the price of going against their doctor's advice, and most people have absolutely no desire to change this personal grooming preference. There are generally no products on the market that are designed specifically to clean earwax from the ear canal. As a result, people will stick almost anything in their ears to get the wax out. The tool of choice for most people is the common cotton swab, which turns out to be a very dangerous tool for inserting into the ear canal to clean out earwax. Cotton swabs can push earwax deeper into the ear canal, thereby causing further wax buildup, pain, itching, a risk of infection, and hearing loss. Another reason why a person shouldn't remove the wax with a cotton swab in particular is that at the end of the ear canal is the eardrum, and the eardrum is much closer to the outside than most people think. A cotton swab pushed too far into the ear canal can easily damage the eardrum, sometimes resulting in permanent hearing loss. For these reasons, a more useful and appealing alternative to a cotton swab is needed.

SUMMARY OF THE INVENTION

The present invention is directed toward a fingertip cleaning apparatus comprising a fingertip receiving portion including a conical wall defining a cavity having an open end configured to allow a fingertip of a user to be inserted into the cavity, the conical wall extending along and surrounding a cone axis, the conical wall forming a cone angle with the cone axis; a gripping portion comprising a flap that extends from the conical wall of the fingertip receiving portion along a grip axis that forms a grip angle with the cone axis; and the grip angle being greater than the once angle.

In other embodiments, the present invention includes a method of cleaning an ear canal of a user comprising: a) inserting at least a portion of a fingertip of a first finger into a cavity of a fingertip cleaning apparatus comprising a fingertip receiving portion and a gripping portion so that: (1) the fingertip receiving portion protrudes from the fingertip and extends along an axis that is inclined relative a fingertip axis along which the fingertip of the first finger extends; and (2) the gripping portion extends adjacent an outer surface of the fingertip of the first finger; and b) inserting the fingertip receiving portion of the fingertip cleaning device into the ear canal.

Other embodiments of the present invention include a fingertip cleaning apparatus comprising a single flexible sheet folded into a three-dimensional configuration comprising: a fingertip receiving portion including a conical wall defining a cavity having an open end configured to allow a fingertip of a user to be inserted into the cavity; and a gripping portion comprising a flap that extends from the conical wall of the fingertip receiving portion.

Other embodiments of the present invention include a fingertip cleaning apparatus comprising a fingertip receiving portion including a conical wall defining a cavity having an open end configured to allow a fingertip of a user to be inserted into the cavity, the conical wall having a first length measured along a cone axis from the open end of the cavity to an apex of the conical wall; a gripping portion comprising a flap that extends from the conical wall of the fingertip receiving portion, the flap having a convex outer surface and a concave inner surface, the flap having a second length measured along a grip axis from the open end of the cavity to a distal-most end of the flap; and the second length being greater than or equal to the first length.

In other embodiments, the present invention includes a fingertip cleaning apparatus comprising a fingertip receiving portion including a conical wall defining a cavity having an open end configured to allow a fingertip of a user to be inserted into the cavity; the conical wall extending along and surrounding a cone axis; and the conical wall comprising: an upper portion comprising an apex and having a first cone angle relative to the cone axis; and a lower portion comprising a lower edge that at least partially defines the open end of the cavity and having a second cone angle relative to the cone axis, the second cone angle being greater than the first cone angle.

Other embodiments of the present invention include a sheet blank for folding into a fingertip cleaning apparatus, the sheet blank comprising a grip blank portion having a grip blank lower edge, a first grip blank side edge extending upward from the lower edge; and a second grip blank side edge extending upward from the grip blank lower edge and being opposite the first grip blank side edge; a fingertip receiving blank portion adjacent the grip blank portion, the fingertip receiving blank portion comprising a first fingertip receiving blank side edge extending upward and outward from the first grip blank side edge, a second fingertip receiving blank side edge opposite the first fingertip receiving blank side edge, the second fingertip receiving blank side edge extending upward and outward from the second grip blank side edge, and an fingertip receiving blank top edge extending between the first and second fingertip receiving blank side edges.

Other embodiments of the present invention include a sheet blank for folding into a fingertip cleaning apparatus, the sheet blank comprising a grip blank portion a grip blank lower edge; a first grip blank side edge extending upward from the lower edge; and a second grip blank side edge extending upward from the grip blank lower edge and being opposite the first grip blank side edge; a fingertip receiving blank portion adjacent the grip blank portion, the fingertip receiving blank portion comprising: a first fingertip receiving blank side edge extending upward and outward from first grip blank side edge; a second fingertip receiving blank side edge opposite the first fingertip receiving blank side edge, the second fingertip receiving blank side edge extending upward and inward from the second grip blank side edge; and an fingertip receiving blank top edge extending between the first and second fingertip receiving blank side edges.

In some embodiments, the present invention includes a package of fingertip cleaning apparatus comprising: a package; a plurality of fingertip cleaning apparatus, each of the fingertip cleaning apparatus comprising: a fingertip receiving portion including a conical wall defining a cavity having an open end configured to allow a fingertip of a user to be inserted into the cavity; a gripping portion comprising a flap that extends from the conical wall of the fingertip receiving portion; the plurality of fingertip cleaning apparatus disposed within the package and arranged in a stack so that the fingertip receiving portions of the plurality of fingertip cleaning apparatus nest within the cavities of adjacent ones of the plurality of fingertip cleaning apparatus.

Other embodiments of the present invention include a fingertip cleaning apparatus comprising: a fingertip receiving portion including a conical wall defining a cavity having an open end configured to allow a fingertip of a user to be inserted into the cavity, the conical wall having an inner surface opposite an outer surface, whereby the conical wall extends along and surrounding a cone axis, the conical wall forming a cone angle with the cone axis and the inner surface defines the cavity; a gripping portion comprising a flap that extends from the conical wall of the fingertip receiving portion along a grip axis that forms a grip angle with the cone axis; and wherein the grip angle being equal to or greater than the once angle, and the inner surface of the conical wall comprises a first material and the outer surface of the conical wall comprises a second material, whereby the first and second materials are different.

Other embodiments of the present invention include a fingertip cleaning apparatus comprising: a fingertip receiving portion including a conical wall defining a cavity having an open end configured to allow a fingertip of a user to be inserted into the cavity, the conical wall having an outer surface, whereby the conical wall extends along and surrounding a cone axis, the conical wall forming a cone angle with the cone axis; a gripping portion comprising a flap that extends from the conical wall of the fingertip receiving portion along a grip axis that forms a grip angle with the cone axis; and wherein the grip angle being equal to or greater than the once angle and the outer surface of the conical wall is pre-treated with an oleophilic agent and a hydrophilic agent.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The foregoing summary, as well as the following detailed description of the exemplary embodiments, will be better understood when read in conjunction with the appended drawings. It should be understood, however, that the invention is not limited to the precise arrangements and instrumentalities shown in the following figures:

FIG. 1 is a front perspective view of a fingertip cleaning apparatus of the present invention;

FIG. 2 is a rear perspective view of the fingertip cleaning apparatus;

FIG. 3 is a rear elevation view of the fingertip cleaning apparatus;

FIG. 4 is a side elevation view of the fingertip cleaning apparatus;

FIG. 5 is a front elevation view of the fingertip cleaning apparatus;

FIGS. 8A-8D is a cross-sectional views of the fingertip cleaning apparatus being along line IX-IX as set forth in FIG. 3;

FIG. 14A is a top view of a sheet blank according to one embodiment of the present invention;

FIG. 14B is a front view of a fingertip cleaning apparatus formed from the sheet blank of FIG. 14A;

FIGS. 21A and 22B illustrate front and sectional views of the fingertip cleaning apparatus according to another embodiment of the present invention;

DETAILED DESCRIPTION OF THE INVENTION

Figures 6A, 6B:
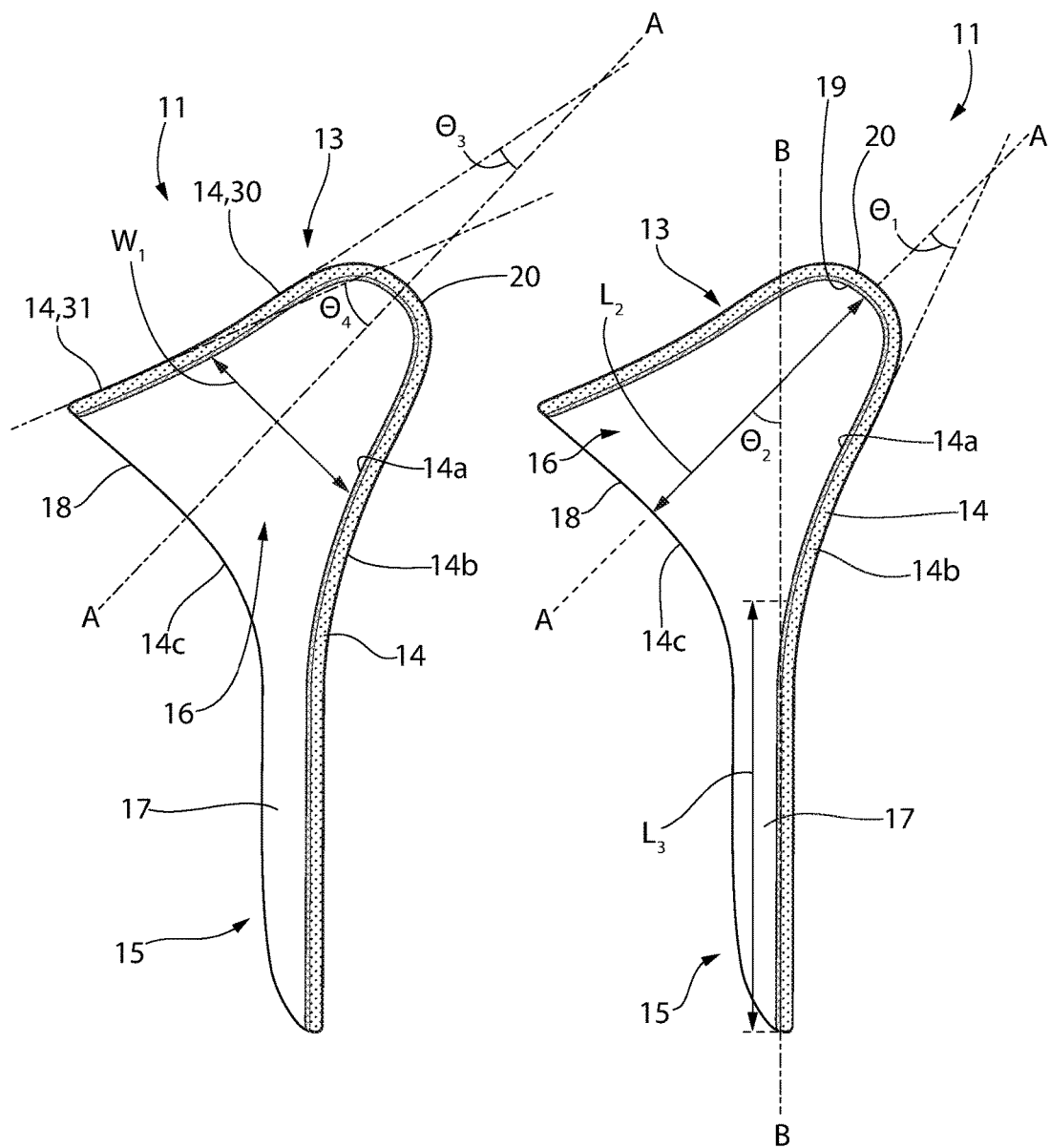
FIGS. 6A-6B is a cross-sectional view of the fingertip cleaning apparatus being along line IX-IX as set forth in FIG. 3.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combinations of features that may exist alone or in other combinations of features; the scope of the invention being defined by the claims appended hereto.

According to the present invention the term "about" refers to a value that is ±3% of the referenced value. According to the present invention the phrase "substantially equal" refers to a value that has a difference in value less than or equal to 3% of the referenced value. According to the present invention, the phrase "substantially parallel" refers to an angle of 0°±2°. The phrases "substantially perpendicular" and "substantially orthogonal" refers to an angle of 90°±2°.

Turning in detail to the drawings, FIGS. 1-6 illustrates a fingertip cleaning apparatus 11 according to the present invention. The fingertip cleaning apparatus 11 is configured to be placed over a user's index finger for cleaning earwax, dirt, and other unwanted contaminants from various external body surfaces. Non-limiting examples of suitable external body surfaces include ear, nose, forehead, neck, armpit, and toes. Although not limited to ear cleaning, the fingertip cleaning apparatus 11 of the present invention will be referred to herein as an "ear cleaning apparatus" 11, which is configured to be placed over a user's index finger for cleaning earwax, dirt, and other unwanted contaminants from the outer part of the ear canal—as described further herein.

The ear cleaning apparatus 11 includes a fingertip receiving portion 13 (also referred to as an "ear insertion portion" or "insertion portion") and a gripping portion 15. The ear cleaning apparatus 11 may comprise a flexible sheet 80, 80a, 80b that is folded into a three-dimensional configuration that forms the fingertip receiving portion 13 and the gripping portion 15—as discussed further herein. In some embodiments, the fingertip receiving portion 13 and the gripping portion 15 are formed from a single flexible sheet 80, 80a, 80b that is folded into the ear cleaning apparatus 11—as discussed further herein.

The ear cleaning apparatus 11 may comprise an inner surface 11a, an outer surface 11b, and an edge 11c—the edge 11 extending between the inner surface 11a and the outer surface 11b. The ear cleaning apparatus 11 may comprise a distal end 1 opposite a proximal end 2. The ear cleaning apparatus 11 may have a length $L_1$ that is measured from the distal end 1 to the proximal end 2. Non-limiting examples of the length $L_1$ may range from about 35 mm to about 85 mm—including all lengths and sub-ranges there-between. In some embodiments, the length $L_1$ may range from about 55 mm to about 70 mm—including all lengths and sub-ranges there-between.

The fingertip receiving portion 13 includes a conical wall 14 defining a cavity 16 having an open end 18 configured to allow a fingertip of a user to be inserted into the cavity 16. The conical wall 14 may comprise an inner surface 14a opposite an outer surface 14b. The conical wall 14 may further comprise a lower edge 14c that extends between the inner surface 14a and the outer surface 14b of the conical wall 14. The conical wall 14 extends along and surrounding a cone axis A-A. The cavity 16 further comprises a closed end 19 that is opposite the open end 18 along the cone axis A-A.

The conical wall 14 forms a cone angle $\varnothing_1$ with the cone axis A-A. The cone angle $\varnothing_1$ may range from about 15° to about 65°—including all angles and sub-ranges there-between. In a preferred embodiments, the cone angle $\varnothing_1$ may range from about 25° to about 50°—including all angles and sub-ranges there-between. In a preferred embodiments, the cone angle $\varnothing_1$ may range from about 35° to about 45°—including all angles and sub-ranges there-between.

The open end 18 of the cavity 16 may be at least partially circumscribed by the lower edge 14c of the conical wall 14. The lower edge 14c may partially define the open end 18 of the cavity 16. As demonstrated by FIG. 6, at least a portion of the lower edge 14c may be oriented substantially perpendicular to the cone axis A-A.

The conical wall 14 may comprise an apex 20. The distal end 1 of the ear cleaning apparatus 11 may comprise the apex 20 of the conical wall 14. The apex 20 may be rounded (also referred to as a "rounded apex") such that distal end 1 of the ear cleaning apparatus 11 does not comprise a point. The closed end 19 of the cavity 16 may be defined by the apex 20 of the conical wall 14. The closed end 19 may form a ceiling of the cavity 16, whereby the ceiling also comprises a rounded geometry.

Referring now to FIG. 6A, in some embodiments the conical wall 14 may comprise an upper portion 30 and a lower portion 31. The upper portion 30 of the conical wall 14 may comprise the apex 20. The lower portion 31 of the conical wall 14 may at least partially define the open end 18 of the cavity 16. In some embodiments, the upper portion may comprise the apex 20 and closed end 19 and extend to the lower portion 31, whereby the lower portion 31 comprises the open end 18. The upper portion may form a first cone angle $Ø_3$ with the cone axis A-A. The lower portion may form a second cone angle $Ø_4$ with the cone axis A-A.

The second cone angle $Ø_4$ of the lower portion 31 of the conical wall 14 may be equal to or greater than the first cone angle $Ø_3$ of the upper portion 30 of the conical wall 14. In some embodiments, the second cone angle $Ø_4$ of the lower portion 31 of the conical wall 14 may be greater than the first cone angle $Ø_3$ of the upper portion 30 of the conical wall 14. A ratio between the second cone angle $Ø_4$ and the first cone angle $Ø_3$ may range from about 1.0:1.0 to about 5.0:1.0—including all ratios and sub-ranges there-between. In other embodiments, the ratio between the second cone angle $Ø_4$ and the first cone angle $Ø_3$ may range from about 1.1:1.0 to about 4.0:1.0—including all ratios and sub-ranges there-between.

Referring to FIG. 6B, the conical wall 14 may have a length $L_2$ as measured along the cone axis A-A from the open end 18 to the apex 20 (or closed end 19) of the cavity 16. The length $L_2$ of the conical wall 14 may range from about 15 mm to about 35 mm—including all lengths and sub-ranges there-between. In a non-limiting example, the length $L_2$ of the conical wall 14 may be about 24 mm.

As demonstrated by FIG. 6A, the cavity 16 may have a width $W_1$ that is the distance between opposite inner surfaces 14a of the conical wall 14 as measured in a direction that is substantially perpendicular to the cone axis A-A. The width $W_1$ of the cavity 16 may range from about 5 mm to about 30 mm—including all widths and sub-ranges there-between. In some embodiments, the width $W_1$ of the cavity 16 may range from about 7 mm to about 20 mm—including all widths and sub-ranges there-between.

The width $W_1$ of the cavity 16 may be non-constant when viewed along the cone axis A-A. The width W1 of the cavity 16 may taper moving in a direction from the open end 18 to the closed end 19 of the cavity 16. The width $W_1$ of the cavity 16 may taper in a linear fashion. In other embodiments, the width $W_1$ of the cavity 16 may taper in a non-linear fashion. The width $W_1$ of the cavity 16 proximate to the open end 18 may be greater than the width $W_1$ of the cavity 16 at the closed end 19. The width $W_1$ proximate the open end 18 of the cavity 16 may be about 20 mm. The width $W_1$ proximate the closed end 19 of the cavity 16 may be about 7 mm.

The conical wall 14 may have a cross-sectional shape that is taken along the cone axis A-A which is circular. In other embodiments, the conical wall 14 may have a cross-sectional shape that is taken along the cone axis A-A which is ovular. In other embodiments, the conical wall 14 may have a cross-sectional shape taken along the cone axis A-A that is polygonal—including but not limited to 3, 4, 5, 6, 7, 8, 9, or 10 distinct sides. The polygonal cross-sectional shape may be a regular polygon (also referred to as an equiangular polygon) or an irregular polygon.

The gripping portion 15 comprises a flap 17. The flap 17 may extend directly from the fingertip receiving portion 13, and it may be formed as an extension of the fingertip receiving portion 13 to have a flat to slightly curved shape. The flap 17 extends from the conical wall 14 of the fingertip receiving portion 13 along a grip axis B-B. The grip axis B-B forms a grip angle $Ø_2$ with the cone axis A-A. The grip angle $Ø_2$ may range from about 15° to about 80°—including all angles and sub-ranges there-between. In a preferred embodiments, the grip angle $Ø_2$ may range from about 25° to about 75°—including all angles and sub-ranges there-between. In a preferred embodiments, the grip angle $Ø_2$ may range from about 40° to about 70°—including all angles and sub-ranges there-between.

The grip angle $Ø_2$ may be greater than or equal to the cone angle $Ø_1$. In some embodiments, the grip angle $Ø_2$ may be substantially equal to the cone angle $Ø_1$—as discussed further herein. In other embodiments, the grip angle $Ø_2$ may be greater than the cone angle $Ø_1$—as discussed further herein. A ratio between the grip angle $Ø_2$ and the cone angle $Ø_1$ may range from about 1.0:1.0 to about 8.0:1.0—including all ratios and sub-ranges there-between. In other embodiments, the ratio between the grip angle $Ø_2$ and the cone angle $Ø_1$ may range from about 1.1:1.0 to about 4.0:1.0—including all ratios and sub-ranges there-between.

The flap 17 may comprise curved transverse cross-sectional profile taken along the grip axis B-B. The flap 17 may comprise an inner surface 17a opposite an outer surface 17b, as well as a side edge 21 extending there-between. The inner surface 17a of the flap 17 may be concave in shape. The outer surface 17b of the flap 17 may be convex in shape.

The side edge 21 of the flap 17 may comprise a first side edge 21a, a second side edge 21b, and a lower edge 21c. The lower edge 21c may extend between the first side edge 21a and the second side edge 21b. The first side edge 21a may extend continuously into the lower edge 21c. The second side edge 21b may extend continuously into the lower edge 21c. The first edge 21a, second side edge 21b, and the lower edge 21c may collectively define an uninterrupted surface that forms the side edge 21 of the flap 17.

Referring to FIG. 6B, the flap 17 may have a length $L_3$ as measured along the grip axis B-B from the open end 18 of the cavity 16 to the distal-most end of the flap (show as the proximal end 2 of the of the ear cleaning apparatus 11 in FIG. 6b). The length $L_3$ of the flap 17 may range from about 30 mm to about 50 mm—including all lengths and sub-ranges there-between. In a non-limiting example, the length $L_3$ of the flap 17 may be about 36 mm.

The length $L_3$ of the flap 17 may be equal to or greater than the length $L_2$ of the conical wall 14. In some embodiments, the length $L_3$ of the flap 17 may be greater than the length $L_2$ of the conical wall 14. A ratio of the length $L_3$ of the flap 17 to the length $L_2$ of the conical wall 14 may range from about 1.0:1.0 to about 3.0:1.0—including all ratios and sub-ranges there-between. In a preferred embodiment, the ratio of the length $L_3$ of the flap 17 to the length $L_2$ of the conical wall 14 may range from about 1.1:1.0 to about 2.5:1.0—including all ratios and sub-ranges there-between.

As demonstrated by FIG. 5, the flap 18 may have a width $W_2$ that is the distance between the first side edge 21a and the second side edge 21b as measured in a direction that is substantially perpendicular to the grip axis B-B. The width $W_2$ of the flap 18 may range from about 20 mm to about 50 mm—including all widths and sub-ranges there-between. In some embodiments, the width $W_2$ of the flap 18 may range from about 20 mm to about 40 mm—including all widths and sub-ranges there-between.

The width $W_1$ of the flap 18 may be non-constant when viewed along the grip axis B-B. The width W1 of the flap 16 may taper moving in a direction from the distal end 1 to the proximal end 2 of ear cleaning apparatus 11. The width $W_2$ of the flap 18 may taper in a linear fashion. In other embodiments, the width $W_2$ of the flap 18 may taper in a non-linear fashion. The width $W_2$ of the flap 18 adjacent the proximal end 2 may be greater than the width $W_2$ of the flap 18 adjacent the insertion portion 13. The width $W_2$ of the flap 18 adjacent the proximal end 2 may be about 30 mm. The width $W_2$ of the flap 18 adjacent the insertion portion 13 may be about 24 mm.

The flap 18 may have a first maximum width $W_{FMAX}$ and the cavity 16 may have a second maximum width $W_{CMAX}$. The first maximum width $W_{FMAX}$ of the flap 18 may be equal to or greater than the second maximum width $W_{CMAX}$ of the cavity 16 In a preferred embodiment, the first maximum width $W_{FMAX}$ of the flap 18 is greater than the second maximum width $W_{CMAX}$ of the cavity 16. A ratio of the first maximum width $W_{FMAX}$ of the flap 18 and the second maximum width $W_{CMAX}$ of the cavity 16 may range from about 1:1 to about 3:1—including all ratios and sub-ranges there-between. In a preferred embodiment, the ratio of the first maximum width $W_{FMAX}$ of the flap 18 to the second maximum width $W_{CMAX}$ of the cavity 16 may range from about 1.1:1 to about 2:1—including all ratios and sub-ranges there-between.

The flap 17 may extend from the conical wall 14 such that the outer surface 17b of the flap 17 is continuous with the outer surface 14b of the conical wall 14 and collectively defining an uninterrupted surface. In some embodiments, the flap 17 may extend from the conical wall 14 such that the outer surface 17b of the flap 17 is continuous with the outer surface 14b of the conical wall 14 and collectively defining an uninterrupted surface that forms the outer surface 11b of the ear cleaning apparatus 11. The uninterrupted outer surface 11b of the ear cleaning apparatus 11 may be smooth.

The side surface 11c of the ear cleaning apparatus 11 may comprise the lower edge 14c of the conical wall 14. The side surface 11c of the ear cleaning apparatus 11 may comprise the side edge 21 of the flap 17. The lower edge 14c of the conical wall 14 may extend into the side edge 21 of the flap 17. In some embodiments, the lower edge 14c of the conical wall 14 may extend continuously into the side edge 21 of the flap 17 to form the side surface 11c of the ear cleaning apparatus 11, whereby the side surface 11c of is continuous and uninterrupted. The first side edge 21a, second side edge 21b, and lower edge 21c of the flap 17 as well as the lower edge 14c of the conical wall 14 may define a continuous edge 11c of the ear cleaning apparatus 11.

Figure 7A:
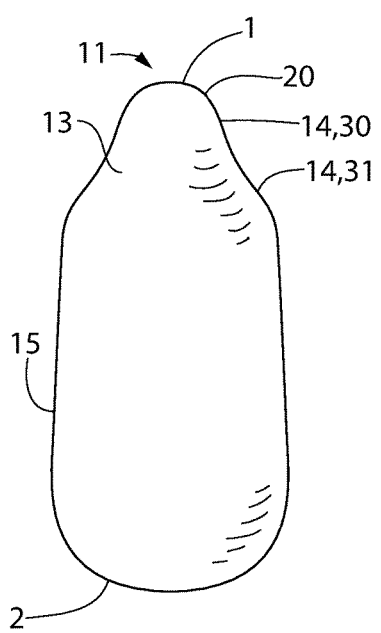
FIGS. 7A-7C are rear, front, and side views of a fingertip cleaning apparatus according to another embodiment of the present invention.
Figure 7B:
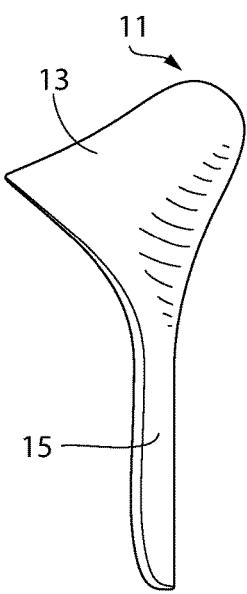
Figure 7C:
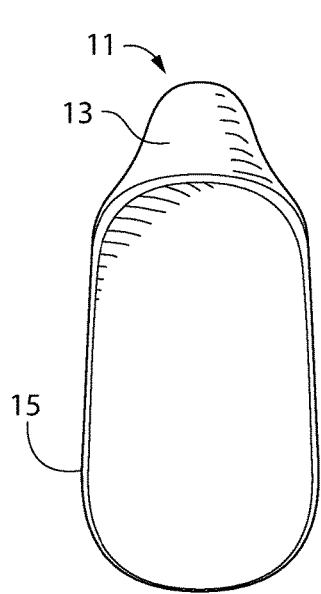
Figure 9A:
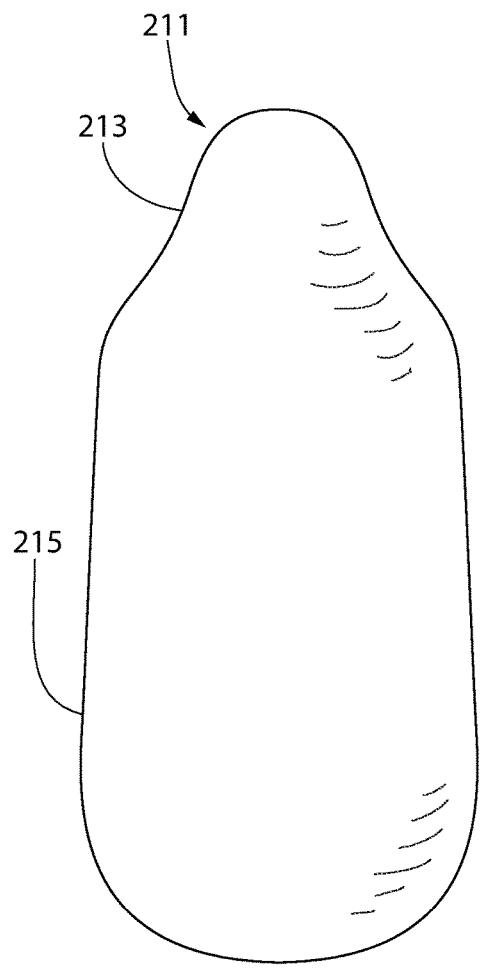
FIG. 9A is rear elevation view of a fingertip cleaning apparatus according to another embodiment of the present invention.
Figure 9B:
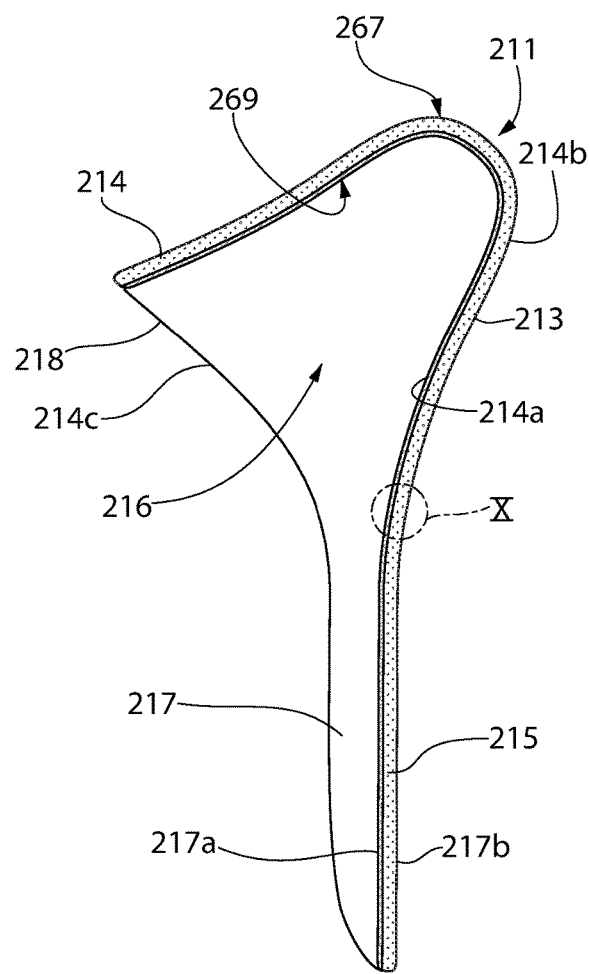
FIG. 9B is cross-sectional view of the fingertip cleaning apparatus of FIG. 9A, the cross-sectional view being along line X-X as set forth in FIG. 9A.

Referring now to FIGS. 7A-7C, another embodiment of the ear cleaning apparatus 11 is provided. As compared to the embodiment shown in FIGS. 1-6, the fingertip receiving portion 13 is formed to have a larger cross-sectional circumference when viewed in a plane which is orthogonal to the cone axis A-A of the fingertip receiving portion 13. The tip of the fingertip receiving portion 13 of this ear cleaning apparatus 11 is also broader than the tip of the fingertip receiving portion 13 of the ear cleaning apparatus 11 of FIGS. 1-6. This ear cleaning apparatus 11 may therefore be made for a user having larger fingers, or alternatively, it may be intended for use by all users, although it would not extend as far into the ear canal during use as would the fingertip receiving portion 13 of the ear cleaning apparatus 11.

Additionally, referring now to FIGS. 8A-8D, demonstrate the change in geometry for the ear cleaning apparatus for various cone angles $\varnothing_1$ and grip angles $\varnothing_2$. As demonstrated in FIG. 8A the cone angles $\varnothing_1$ and grip angles $\varnothing_2$ may be substantially equal. As demonstrated in FIG. 8B, the cone angles $\varnothing_1$ may be about 35°, whereby the grip angle $\varnothing_2$ is greater than the cone angle $\varnothing_1$. As demonstrated in FIG. 8C, the cone angles $\varnothing_1$ may be about 40°, whereby the grip angle $\varnothing_2$ is greater than the cone angle $\varnothing_1$. As demonstrated in FIG. 8D, the cone angles $\varnothing_1$ may be about 45°, whereby the grip angle $\varnothing_2$ is greater than the cone angle $\varnothing_1$.

The ear cleaning apparatus 11 of the present invention may be formed from a single or multi-layer construction formed from material that may include cotton (e.g., non-woven or woven fabric); non-woven synthetic fiber (e.g., polypropylene, nylon, and other similar materials); other organic fibers (e.g., bamboo, hemp, modal, and other plant-based fibers), bond paper (e.g., thin card or heavy paper); formed paper pulp; thermoformed plastic (e.g., styrene, polyethylene terephthalate, polyurethane, and other similar materials); thermoformed foamed rubber (e.g., ethylene vinyl acetate, polyvinyl chloride, and other similar materials); molded plastic (e.g., polypropylene, acrylonitrile butadiene styrene, and other similar materials). The fibers may be quilted to form a macroscopic texture.

Referring now to FIGS. 10A-11B, a multi-layered ear cleaning apparatus 211 of the present invention will be discussed in greater detail. The ear cleaning apparatus 211 is similar to ear cleaning apparatus 11 except as described herein below. The description of the ear cleaning apparatus 11 above generally applies to the ear cleaning apparatus 211 described below except with regard to the differences specifically noted below. A similar numbering scheme will be used for the ear cleaning apparatus 211 as with the ear cleaning apparatus 11 except that the 200-series of numbers will be used.

The ear cleaning apparatus 211 may comprise at least two layers 267, 269 that include an outer layer 267 and an inner layer 269. The outer layer 267 may form the outer surface 211b of the ear cleaning device 211 and the inner layer 269 may form the inner surface 211a of the ear cleaning device. The edge 211c of the ear cleaning device 211 may comprise both the outer layer 267 and the inner layer 269.

The outer layer 267 may be formed of cleaning surface materials, and the inner layer 269 formed of materials which provide desired structure and/or rigidity to the ear cleaning apparatus 211. The inner layer 269 may further be referred to as the "structural layer." The outer layer 267 and the inner layer 26 may be directly or indirectly coupled or bonded together in any appropriate manner for the materials used for the respective layers. In certain embodiments, the inner layer 269 may be included for additional purposes, such to provide a scrubbing surface, which is characterized by being a coarser and/or less flexible which is also non-absorbent. In contrast, the outer layer 267 is provided and intended primarily for a soft wiping surface which may be used dry or wet, and when used wet, the material is able to absorb moisture for enhanced wiping/cleaning. The differences between a scrubbing surface and a wiping surface are illustrated more in some of the embodiments described below.

Figure 10A:
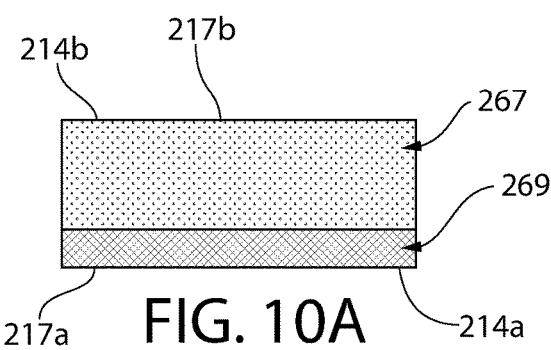
FIGS. 10A and 10B are different embodiments of the close up view of the section X of the fingertip cleaning apparatus set forth in FIG. 9B.
Figure 10B:
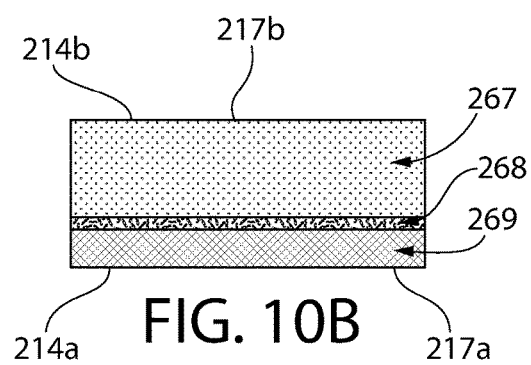

As shown in FIG. 10B, the multi-layer construction of the ear cleaning apparatus 211 may include three layers, 267, 268, 269. These three layers include the inner layer 267, the outer layer 269, as well as an intermediate layer 268 positioned there-between. The intermediate layer 43 may be a barrier layer and formed of materials which prevent moisture penetration and/or evaporation from passing between the inner and outer surfaces 211a, 211b of the ear cleaning apparatus 211. The inner layer 269, intermediate layer 268, and outer layer 267 may be directly or indirectly coupled or bonded together in any appropriate manner for the materials used for the respective layers.

Non-limiting examples of material suitable as the outer layer 267 of the ear cleaning apparatus 211 may include: cotton (e.g., non-woven or woven fabric); non-woven synthetic fiber (e.g., polypropylene, nylon, rayon, and other similar materials); other organic fibers (e.g., bamboo, hemp, modal, and other plant-based fibers). Other types of material may also be used for the outer layer 267. The fibers may be formed by melt-blowing or as spun-lace. The melt-blown fiber may have a weight ranging from about 20 g/m to about 40 g/m—including all weight and sub-ranges there-between. The spun-lace fiber may have a weight ranging from about 40 g/m to about 80 g/m—including all weight and sub-ranges there-between. In a preferred embodiment, the fiber is spun-lace fiber.

For the intended use of cleaning the ear canal and other parts of the ear, it is generally desirable to have the material for the outer layer of a fingertip cleaner selected for absorbency and softness.

Non-limiting examples of materials suitable as the inner layer 267 of the ear cleaning apparatus 211 include: bond paper (e.g., thin card or heavy paper); formed paper pulp; thermoformed plastic (e.g., styrene, polyethylene terephthalate, and other similar materials); thermoformed foamed rubber (e.g., ethylene vinyl acetate, polyvinyl chloride, and other similar materials); molded and fibrous plastic (e.g., polypropylene, polyurethane, acrylonitrile butadiene styrene, and other similar materials).

A non-limiting example of a material suitable as the inner layer 267 include non-woven fabric formed from spun-bonded polypropylene having a weight ranging from about 10 gm/to about 65 g/m, and more specifically about 15 g/m to about 60 g/m—including all weight and sub-ranges there-between. Another non-limiting example of a material suitable as the inner layer 267 include non-woven fabric formed from spun-bonded polypropylene that is coated with polyethylene having a weight ranging from about 80 g/m to about 120 g/m, and more specifically about 90 g/m to about 115 g/m—including all weight and sub-ranges there-between.

Another non-limiting example of a material suitable as the inner layer 267 includes thermoplastic elastomer film. The film is continuous and is suitable as a moisture barrier. Another non-limiting example of a material suitable as the inner layer 267 includes polyurethane film. The film is continuous and is suitable as a moisture barrier while still being air-permeable.

Other types of material may also be used for the inner layer 269. For the intended use of an ear cleaning apparatus 211, it is generally desirable to have the material for the inner layer 269 selected to provide a desired amount of stiffness and/or to provide a desired texture which may be used for scrubbing. In certain embodiments, and by selection of an appropriate material, the inner layer 269 may also serve as a barrier layer.

Non-limiting examples of material suitable as the barrier layer of a multi-layered ear cleaning apparatus 211 include: thermoplastic elastomer (e.g., thermoplastic elastomers, rubber, and other similar materials); extruded film (e.g., low density polyethylene, polyvinyl chloride, and other similar materials). Other types of material may also be used for the barrier layer.

Figure 23:
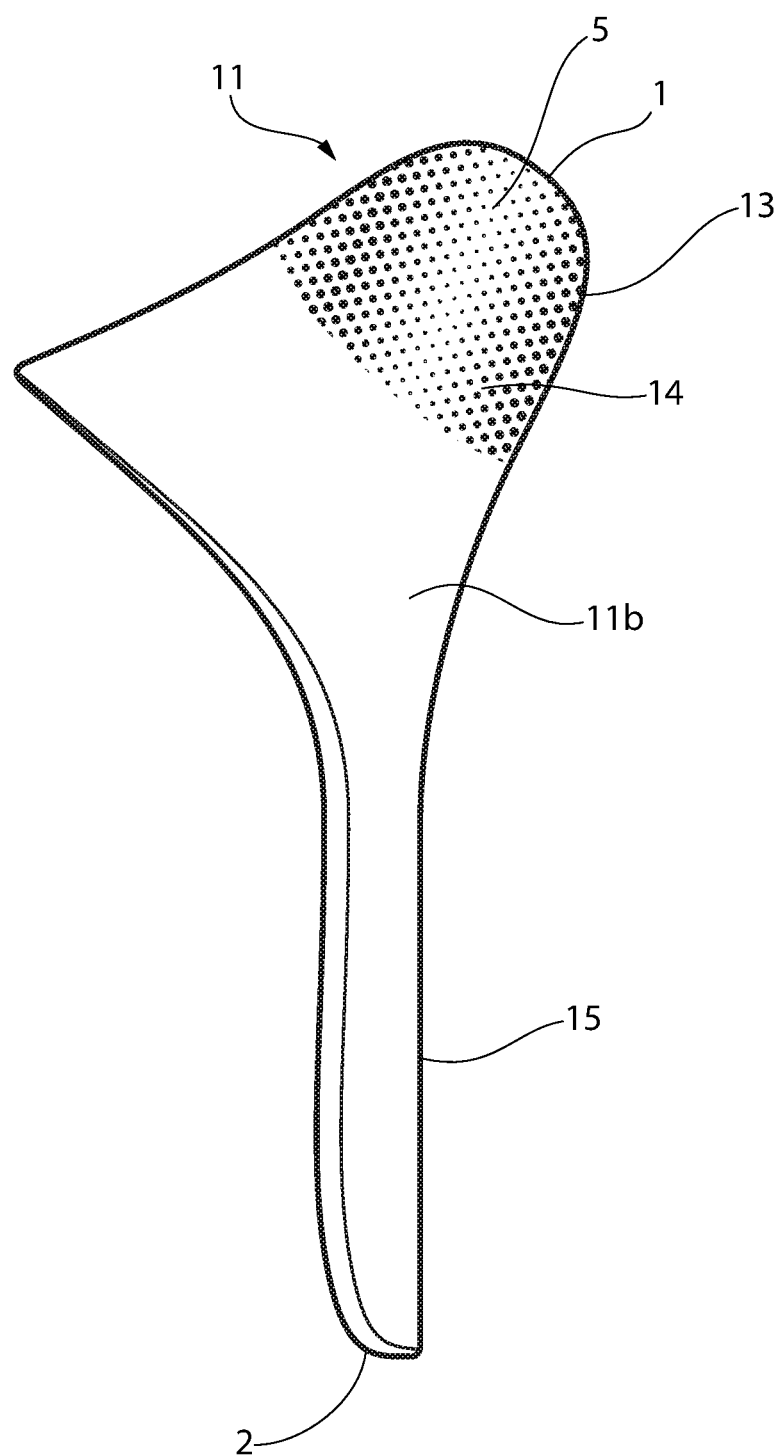
FIG. 23 is a side view of the fingertip cleaning apparatus of the present invention.

Referring now to FIG. 23, the ear cleaning apparatus of the present invention may have a textured surface 5 on the fingertip receiving portion 13, whereby the texture surface 5 is present on the outer surface 11b of ear cleaning device 11. The textured surface 5 may be imparted to the outer surface 11b of the ear cleaning apparatus 11 on the fingertip receiving portion 13 as part of the manufacturing process. The texture may have any desirable pattern—including a plurality of columns, dots, or pyramids that impart the textured surface. The texture 5 of the fingertip receiving portion 13 is a macro structure texture 5 which overlays, and is independent of, the micro structure texture of the material used to construct the fingertip receiving portion 13. For example, the macro structure texture is shown as a plurality of dimples, whereas for an fingertip receiving portion 13 formed out of non-woven cotton, the micro structure texture results from the cotton fibers themselves.

Figure 11A:
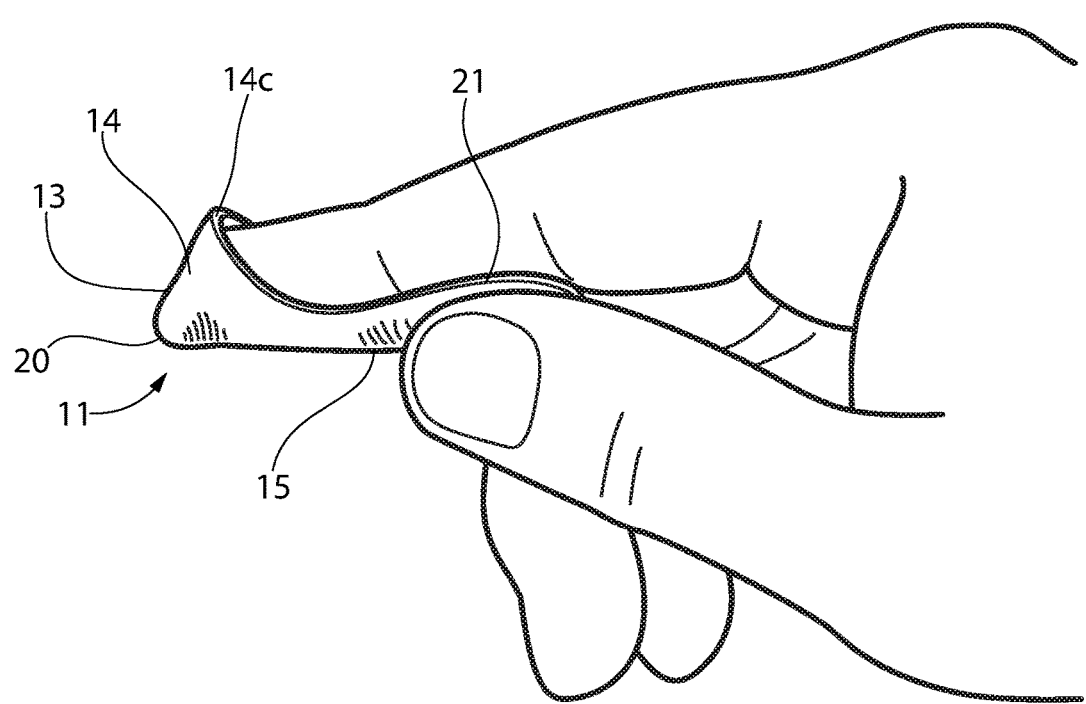
FIGS. 11A and 11B illustrates different grips which may be used with the fingertip cleaning apparatus of the present invention.
Figure 11B:
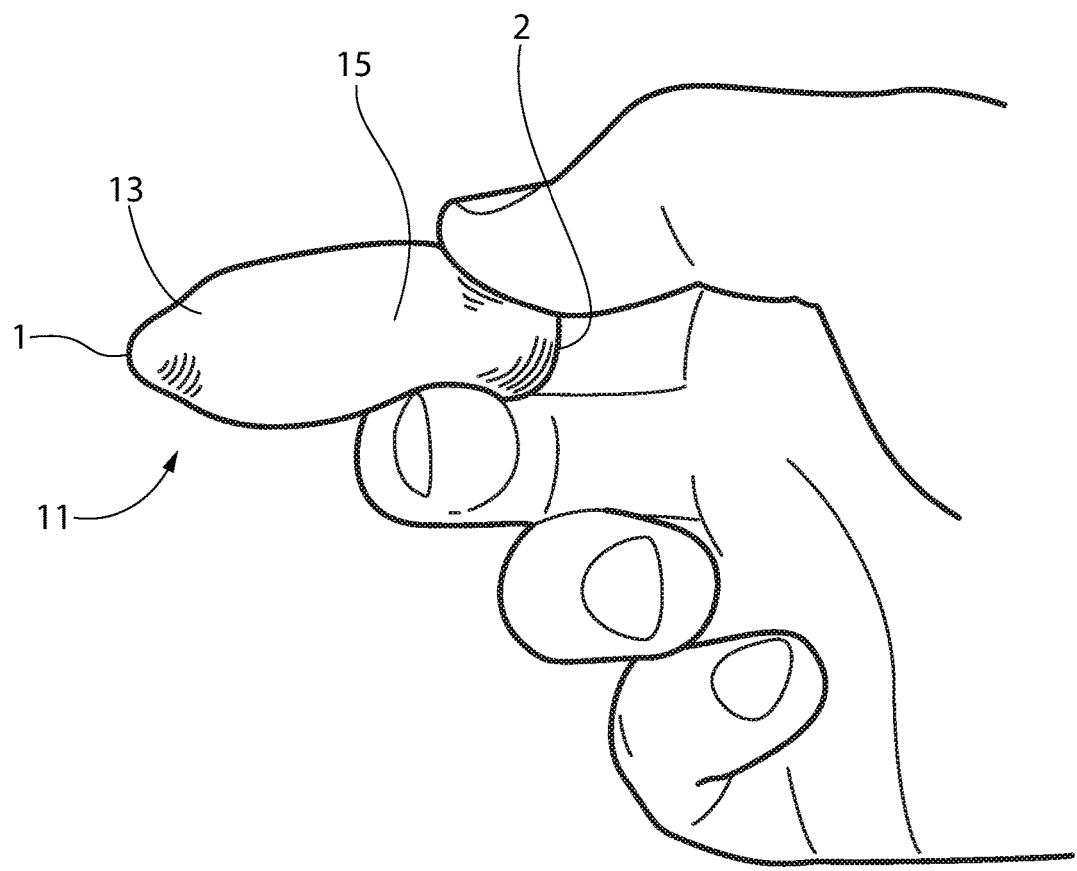

Referring now to FIGS. 11A and 11B, the fingertip receiving portion 13 is formed to fit at least partially over the fingertip to cover the tip of the fingernail. Specifically, the fingernail is inserted into the cavity 16 of the fingertip receiving portion 13. Covering the fingernail is important when cleaning the outer ear canal to avoid unwanted scratches within the ear canal which might be caused by the fingernail. In certain embodiments, the fingertip receiving portion 13 may cover just the tip of the fingernail, and in certain other embodiments, the fingertip receiving portion 13 may cover more of the fingernail, up to the entire fingernail. In certain other embodiments, the fingertip receiving portion 13 may cover even more of the fingertip, up to about the first knuckle. By covering only part of the fingertip, the ear cleaning apparatus 11 is easier to place on and remove from the finger. Also, this reduces the amount of material needed to construct the ear cleaning apparatus 11.

When the ear cleaning apparatus 11 is seated on the forefinger of a user, the gripping portion 15 extends down the finger to at least past the first knuckle. In certain embodiments, the gripping portion 15 may extend to between the first knuckle and up to and including the second knuckle. In certain other embodiments, the gripping portion 15 may extend beyond the second knuckle. When the fingertip receiving portion 13 is seated on the tip of a user's index finger, the user may grip the gripping portion 15 between the thumb and index finger, as shown in FIG. 12A. Alternatively, the user may choose to grip the gripping portion 15 using both the thumb and the middle finger pressed against the index finger, as shown in FIG. 12B. The overall width $W_2$ of the gripping portion 15 is such that it covers at least one side of the typical user's index finger. This may mean that the ear cleaning apparatus 11 may be produced in different sizes to accommodate users' different sizes of fingers.

Figure 12:
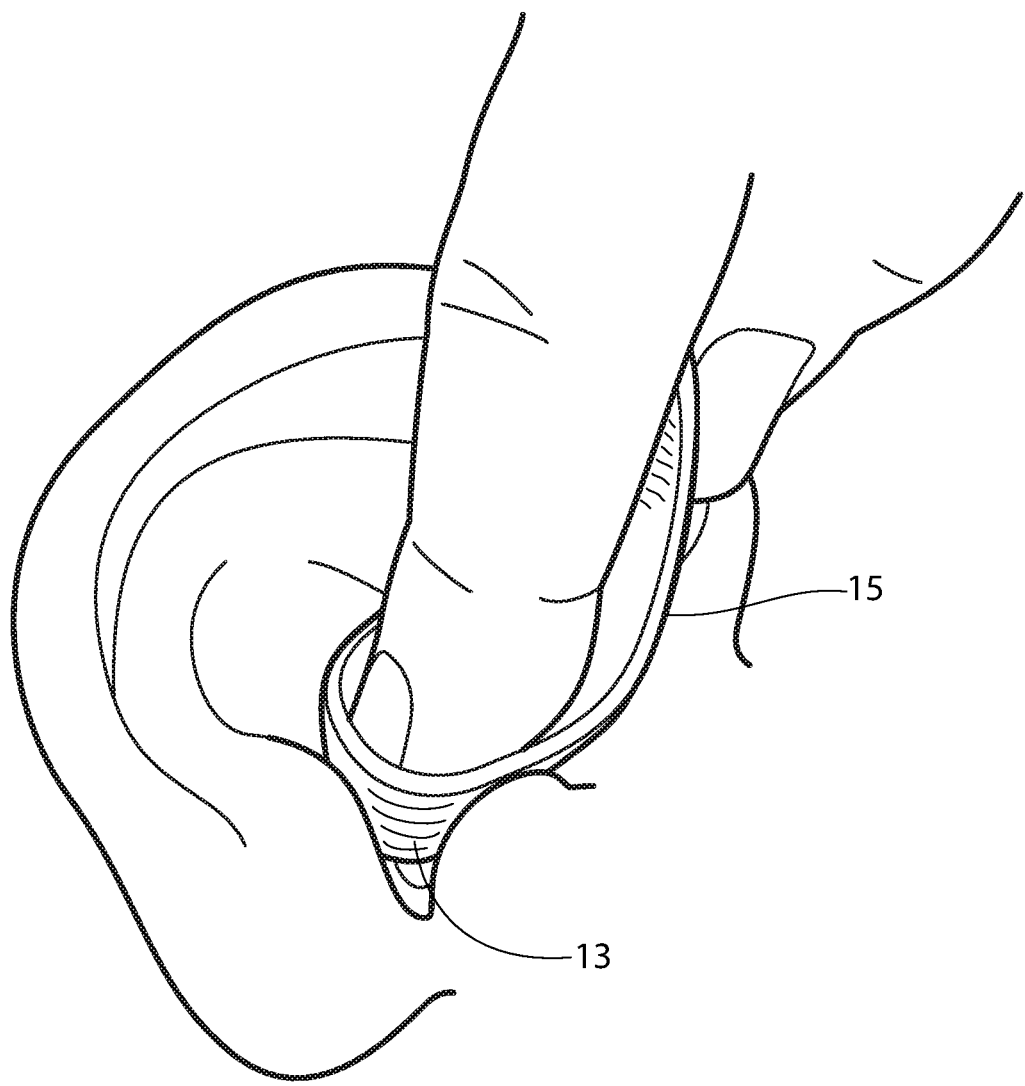
FIG. 12 is the fingertip cleaning apparatus of the present invention being used to clean the ear canal.

Referring now to FIG. 12, the ear cleaning apparatus 11 may have the fingertip receiving portion 13 placed over the tip of a user's index finger, with the gripping portion 15 gripped between the thumb and index finger. Specifically, the user may insert at least a portion of a fingertip of a first finger into the cavity 16 of the ear cleaning apparatus 11 comprising the fingertip receiving portion 13 and the gripping portion 15 so that: (1) the fingertip receiving portion 13 protrudes from the fingertip and extends along the cone axis A-A that is inclined relative a cone axis B-B (also referred to as the "fingertip axis") along which the fingertip of the first finger extends; and (2) the gripping portion 15 extends adjacent an outer surface of the fingertip of the first finger; and inserting the fingertip receiving portion 13 of the ear cleaning device 11 into the ear canal. Additionally, the user grasps the gripping portion 15 of the ear cleaning apparatus 11 between the surface of the fingertip of the first finger and a surface of a second finger during said inserting.

During use, the user straightens their index finger and positions it to be approximately axially aligned with the ear canal, i.e., and axis of the straightened index finger is spatially near and approximately parallel to an axis of the ear canal, with the fingertip receiving portion 13 placed within the outer ear canal. With the ear cleaning apparatus in position and the user having their fingers positioned thusly, the user may rotate their hand about the axis of the straightened index finger to clean the outer ear canal with the rotating motion imparted to the fingertip receiving portion 13. The fingertip receiving portion 13 will extend into the ear canal only slightly further than the tip of the user's index finger. This provides a safe method for ear cleaning. As will be discussed in connection with other embodiments below, the fingertip receiving portion 13 may be constructed with different degrees of stiffness. Embodiments which include a more flexible fingertip receiving portion 13, such as one that is formed solely from a woven material, will have limited reach into the ear canal beyond the tip of the user's finger. In contrast, embodiments which include an fingertip receiving portion 13 formed from a less flexible material will be able to reach further into the ear canal for purposes of cleaning. However, in such embodiments, the shape of the fingertip receiving portion 13 is such that the rounded end of the fingertip receiving portion 13 cannot reach the eardrum for the typical user when the ear cleaning apparatus 11 is used as described herein.

Figure 13:
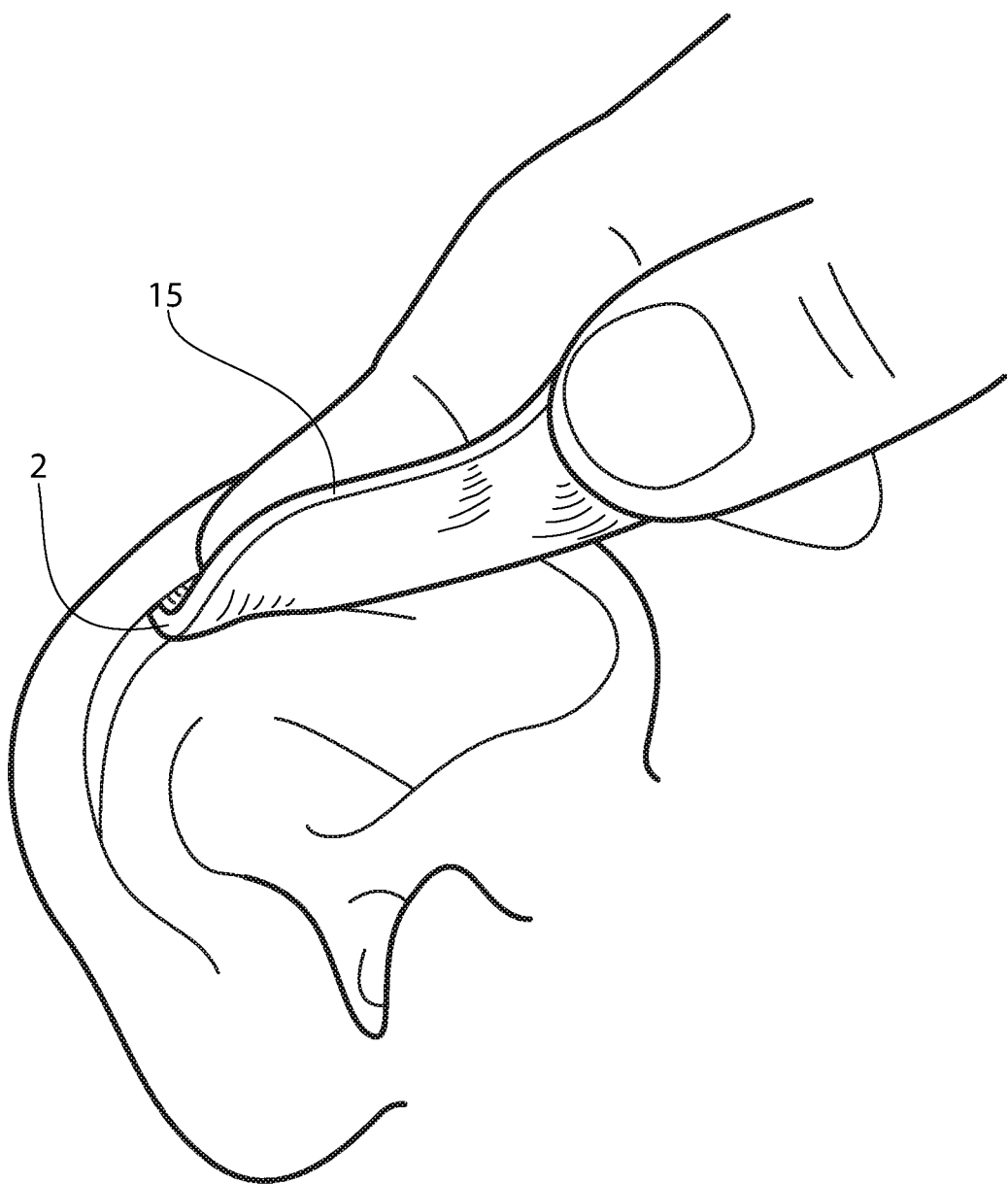
FIG. 13 illustrates the fingertip cleaning apparatus of the present invention being used to clean the auricle.

FIG. 13 illustrates a second use for the ear cleaning apparatus 11. In this use, the gripping portion 15 may be gripped with the proximal end 2 toward to tip of the index finger so that the surface of the gripping portion 15 may be used to wipe the auricle part of the ear. This may be done to help remove any dirt or waxy residue which may have migrated from the outer ear canal onto the auricle.

Referring now to FIGS. 14A, 14B, 15A, and 15B, the ear cleaning apparatus 11 may comprise a flexible sheet 80, 80a, 80b that is folded into a three-dimensional configuration that forms the fingertip receiving portion 13 and the gripping portion 15. In some embodiments, the fingertip receiving portion 13 and the gripping portion 15 are formed from a single flexible sheet 80, 80a, 80b that is folded into the ear cleaning apparatus 11. The ear cleaning apparatus 11 maintains the three-dimensional configuration even in an unused state when the cavity 16 is empty. The flexible sheet 80 (also referred to as a "sheet blank") may comprise a grip blank portion 40 and a fingertip receiving blank portion 50 that is adjacent to the grip blank portion 40.

Referring now to FIGS. 14A and 14B, a first embodiment of the flexible sheet 80, 80a, the grip blank portion 40, 40a may comprises a grip blank lower edge 41 as well as a first grip blank side edge 42 that is opposite a second grip blank side edge 43. The first grip blank side edge 42 extends upward from the grip blank lower edge 41. The second grip blank side edge 43 extends upward from the grip blank lower edge 41. The grip blank lower edge 41 may be convex or flat in shape. The grip blank portion 40, 40a may have a width $W_2$ that is substantially equal to the width $W_2$ of the flap 18 of the ear cleaning apparatus 11.

According to the first embodiment of the flexible sheet 80, 80a, the fingertip receiving blank portion 50, 50a may comprise a first fingertip receiving blank side edge 52 opposite a second fingertip receiving blank side edge 53. The first fingertip receiving blank side edge 52 may extend upward and outward from the first grip blank side edge 42. The second fingertip receiving blank side edge 53 may extend upward and outward from the second grip blank side edge 43. The fingertip receiving blank portion 50, 50a may further comprise a fingertip receiving blank top edge 51 that extends between the first and second fingertip receiving blank side edges 52, 53. The fingertip receiving blank portion 50, 50a may have a maximum width $W_3$ that is greater than the width $W_2$ of the flap 18 of the ear cleaning apparatus 11.

The flexible sheet 80, 80a may further comprise a central blank axis D-D. The central blank axis D-D may intersect both the grip blank lower edge 41 and the fingertip receiving blank top edge 51. The flexible sheet 80, 80a may be symmetric about the central blank axis D-D. The grip blank lower edge 41 may be symmetrical about the central blank axis D-D. The grip blank lower edge 41 may extend between the first and second grip blank side edges 42, 43 in a direction that is substantially perpendicular to the central blank axis D-D. The fingertip receiving blank top edge 51 may be symmetrical about the central blank axis D-D. The fingertip receiving blank top edge 51 may extend between the first and second fingertip receiving blank side edges 52, 53 in a direction that is substantially perpendicular to the central blank axis D-D.

The flexible sheet 80, 80a may have a length $L_1$ that measured along a direction that is substantially parallel to the central axis C-C and substantially equal to the length $L_1$ of the ear cleaning apparatus 11.

The first grip blank side edge 42 and the second grip blank side edge 43 may have an edge profile that is mirrored about the central blank axis D-D. The first fingertip receiving blank side edge 52 and the second fingertip receiving blank side edge 53 may have an edge profile that is mirrored about the central blank axis D-D.

The first grip blank side edge 42 may extend between the grip blank lower edge 41 and the first fingertip receiving blank side edge 52 such that the first grip blank side edge 42 forms a linear or curved profile. The second grip blank side edge 43 may extend between the grip blank lower edge 41 and the second fingertip receiving blank side edge 53 such that the second grip blank side edge 43 forms a linear or curved profile.

The first fingertip receiving blank side edge 52 may extend between the first grip blank side edge 42 and the fingertip receiving blank top edge 51 such that the first fingertip receiving blank side edge 52 forms a linear or curved profile. The second fingertip receiving blank side edge 53 may extend between the second grip blank side edge 43 and the fingertip receiving blank top edge 51 such that the second fingertip receiving blank side edge 53 forms a linear or curved profile.

The first fingertip receiving blank side edge 52 may diverge from the central blank axis D-D with increasing distance from first grip blank side edge 43. The second fingertip receiving blank side edge 53 may diverge from the central blank axis D-D with increasing distance from second grip blank side edge 43. The first fingertip receiving blank side edge 52 may diverge from the central blank axis D-D when measured along a direction parallel to the central axis C-C and extending from the grip blank lower edge 41 to the fingertip receiving blank top edge 51. The second ear 1 insertion blank side edge 53 may diverge from the central blank axis D-D when measured along a direction extending from the grip blank lower edge 41 to the fingertip receiving blank top edge 51.

The first grip blank side edge 42 may be substantially parallel to the central blank axis D-D. The second grip blank side edge 43 may be substantially parallel to the central blank axis D-D. In other embodiments each of the first and second grip blank side edges 42, 43 may independently diverge from central blank axis D-D with increasing distance from the grip blank lower edge 41 toward the fingertip receiving blank top edge 51. In such embodiments, the first and second grip blank side edges 42, 43 may diverge from central blank axis D-D at an angle that is less than the angle at which each of the first and second fingertip receiving blank side edges 52, 53 diverge from the central blank axis D-D.

Figure 15A:
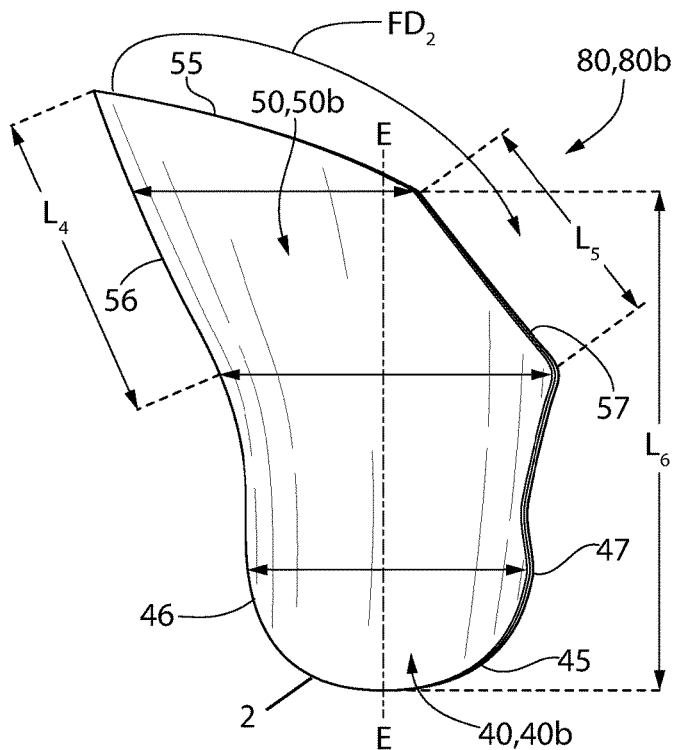
FIG. 15A is a top view of a sheet blank according to another embodiment of the present invention.
Figure 15B:
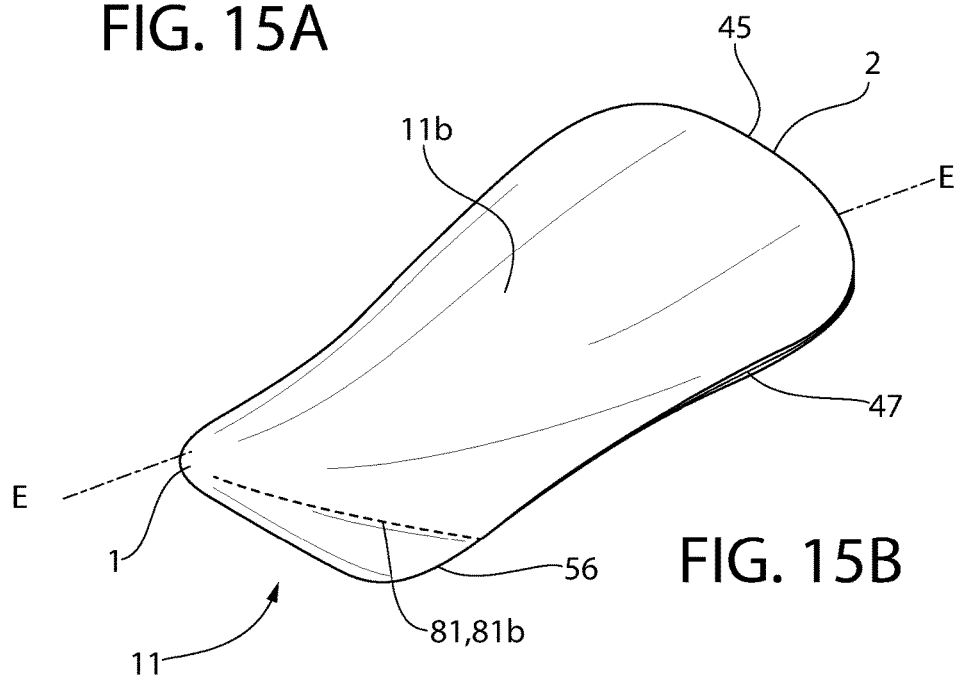
FIG. 15B is a rear perspective view of a fingertip cleaning apparatus formed from the sheet blank of FIG. 15A.

Referring now to FIGS. 15A and 15B, a second embodiment of the flexible sheet 80, 80b, the grip blank portion 40, 40b may comprises a grip blank lower edge 45 as well as a first grip blank side edge 46 that is opposite a second grip blank side edge 47. The first grip blank side edge 46 extends upward from the grip blank lower edge 45. The second grip blank side edge 47 extends upward from the grip blank lower edge 45. The grip blank lower edge 45 may be convex or flat in shape.

According to the second embodiment of the flexible sheet 80, 80b, the fingertip receiving blank portion 50, 50b may comprise a first fingertip receiving blank side edge 56 opposite a second fingertip receiving blank side edge 57. The first fingertip receiving blank side edge 56 may extend upward and outward from the first grip blank side edge 46. The second fingertip receiving blank side edge 57 may extend upward and inward from the second grip blank side edge 47. The fingertip receiving blank portion 50, 50a may further comprise an fingertip receiving blank top edge 55 that extends between the first and second fingertip receiving blank side edges 56, 57.

The flexible sheet 80, 80b may further comprise a central blank axis E-E. The central blank axis E-E may intersect both the grip blank lower edge 45 and the fingertip receiving blank top edge 55. The flexible sheet 80, 80b may be asymmetric about the central blank axis E-E. The grip blank lower edge 45 may be asymmetrical or symmetrical about the central blank axis E-E. The fingertip receiving top edge 55 may be asymmetrical about the central blank axis E-E. The first fingertip receiving blank side edge 56 and the fingertip receiving top edge 55 may be located on the same side of the central blank axis E-E.

The grip blank lower edge 45 may extend between the first and second grip blank side edges 46, 47 in a direction that is substantially perpendicular to the central blank axis E-E. The fingertip receiving blank top edge 55 may extend between the first and second fingertip receiving blank side edges 56, 57 in a direction that is substantially oblique to the central blank axis E-E. The fingertip receiving blank top edge 55 may be inclined relative to the central blank axis E-E such that the fingertip receiving blank top edge 55 extends away from the grip blank lower edge 45 as the fingertip receiving blank top edge 55 approaches the central blank axis E-E.

The first fingertip receiving blank side edge 56 has a length $L_4$ as measured between the fingertip receiving blank top edge 55 and the first grip blank side edge 46. The length $L_4$ of the first fingertip receiving blank side edge 56 may range from about 25 mm to about 35 mm. The length $L_4$ of the first fingertip receiving blank side edge 56 may be about 36 mm. The second fingertip receiving blank side edge 57 has a length $L_5$ as measured between the fingertip receiving blank top edge 55 and the second grip blank side edge 47. The length $L_5$ of the second fingertip receiving blank side edge 57 may range from about 15 mm to about 25 mm. The length $L_4$ of the first fingertip receiving blank side edge 56 may be about 25 mm.

According to the second embodiment of the flexible sheet 80, 80b, the length $L_4$ of the first fingertip receiving blank side edge 56 is greater than the length $L_5$ of the second fingertip receiving blank side edge 57. A ratio of the length $L_4$ of the first fingertip receiving blank side edge 56 to the length $L_5$ of the second fingertip receiving blank side edge 57 may range from about 10.0:1.0 to about 1.1:1—including all ratios and sub-ranges there-between. In a preferred embodiment, the ratio of the length $L_4$ of the first fingertip receiving blank side edge 56 to the length $L_5$ of the second fingertip receiving blank side edge 57 may range from about 3.0:1.0 to about 1.5:1—including all ratios and sub-ranges there-between.

The flexible sheet 80, 80b according to this embodiment may further comprise a length $L_6$ that extends from a transition point that exists between the insertion grip blank top edge 55 and the second fingertip receiving blank side edge 57 and the grip blank lower edge 45. The length $L6$ may be greater than each of the length $L_4$ of the first fingertip receiving blank side edge 56 and the length $L_5$ of the second fingertip receiving blank side edge 57.

The first grip blank edge 46 and the second grip blank edge 47 may have an edge profile that is mirrored about the central blank axis E-E. In other embodiments, the first grip blank edge 46 and the second grip blank edge 47 may have an edge profile that is not mirrored (i.e., asymmetrical) about the central blank axis E-E. The first fingertip receiving blank side edge 56 and the second fingertip receiving blank side edge 57 may have an edge profile that is not mirrored about the central blank axis E-E.

The first grip blank side edge 46 may extend between the grip blank lower edge 45 and the first fingertip receiving blank side edge 56 such that the first grip blank side edge 46 forms a linear or curved profile. The second grip blank side edge 47 may extend between the grip blank lower edge 45 and the second fingertip receiving blank side edge 57 such that the second grip blank side edge 47 forms a linear or curved profile.

The first fingertip receiving blank side edge 56 may extend between the first grip blank side edge 46 and the fingertip receiving blank top edge 55 such that the first fingertip receiving blank side edge 56 forms a linear or curved profile. The second fingertip receiving blank side edge 57 may extend between the second grip blank side edge 47 and the fingertip receiving blank top edge 55 such that the second fingertip receiving blank side edge 57 forms a linear or curved profile.

The first fingertip receiving blank side edge 56 may diverge from the central blank axis E-E with increasing distance from first grip blank side edge 46. The second fingertip receiving blank side edge 57 may converge toward the central blank axis E-E with increasing distance from second grip blank side edge 47. The first fingertip receiving blank side edge 56 may diverge from the central blank axis E-E when measured along a direction parallel to the central axis E-E and extending from the grip blank lower edge 45 to the fingertip receiving blank top edge 55. The second fingertip receiving blank side edge 57 may converge toward the central blank axis E-E when measured along a direction extending from the grip blank lower edge 45 to the fingertip receiving blank top edge 55.

The first grip blank side edge 46 may be substantially parallel to the central blank axis E-E. The second grip blank side edge 47 may be substantially parallel to the central blank axis E-E. In other embodiments each of the first and second grip blank side edges 46, 47 may independently diverge from central blank axis E-E with increasing distance from the grip blank lower edge 45 moving toward the fingertip receiving blank top edge 55. In such embodiments, the first grip blank side edge 46 may diverge from central blank axis E-E at an angle that is less than the angle at which each of the first fingertip receiving blank side edge 56 diverges from the central blank axis E-E.

Figure 18:
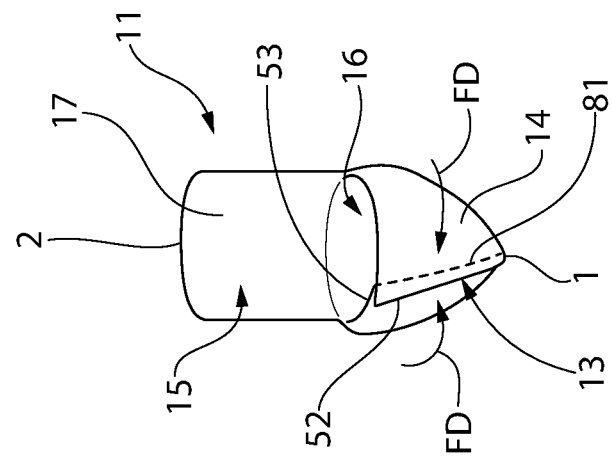
FIGS. 16-18 illustrate a method of forming the fingertip cleaning apparatus of the present invention.
Figure 17:
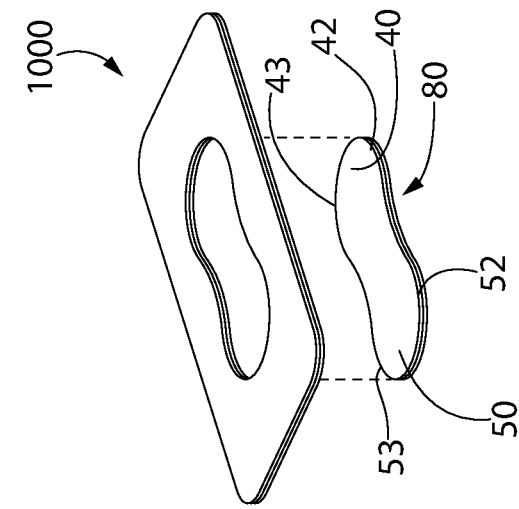
Figure 16:
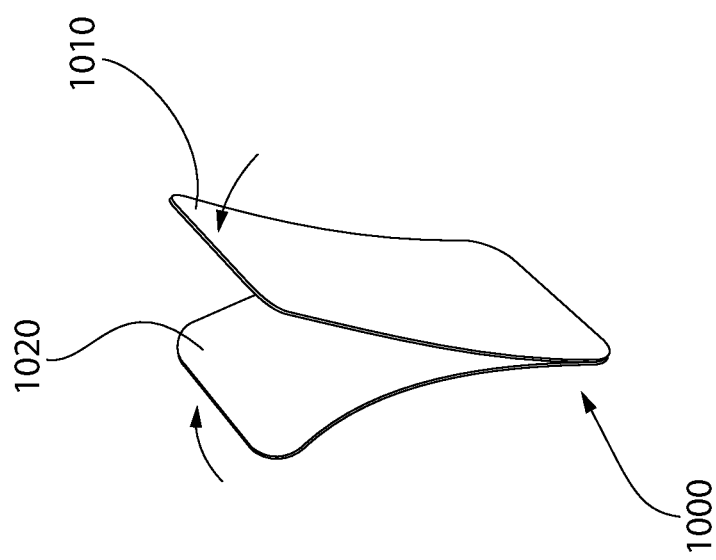

Referring now to FIGS. 16-18, the ear cleaning apparatus of the present invention may be produced from one or more laminate sheets 1000 of material—as discussed further herein. The laminate sheets 1000 may be formed by laminating together a first sheet of material 1010 and a second sheet of material 1020. The first sheet of material 1010 may be formed from the same material as the outer layer 267 of the multi-layered ear cleaning apparatus 211. The second sheet of material 1020 may be formed from the same material as the inner layer 269 of the multilayered ear cleaning apparatus 211. Although not pictured, a third sheet of material may be positioned between the first and second sheets 1010, 1020 of material, whereby the third sheet is formed from the same material as the barrier layer 268 of the multilayered ear cleaning apparatus 211.

Referring now to FIG. 17, once the first, second and/or third sheets of material are laminated together to form the laminate sheet 1000, one or more of the sheet blanks 80 can be cut from the laminate sheet 1000. The sheet blanks 80 may be cut according to any suitable process including, but not limited to, die cutting, roll cutting, and the like. Referring now to FIG. 18, once the sheet blank 80 is cut from the laminate sheet 1000, the fingertip receiving blank portion 50 may be folded along a fold direction FD to form the fingertip receiving portion 13.

Referring now to FIGS. 14A and 14B, according to some embodiments the fingertip receiving blank portion 50a may be folded along a fold direction $FD_1$ such that the first fingertip receiving blank side edge 52 meets the second fingertip receiving blank side edge 53 at a distance that is substantially equidistance between the first and second fingertip receiving blank side edges 52, 53. Meeting the first and second fingertip receiving portion blank side edges 52, 53 may create a partial overlap therein.

Once folded along the fold direction $FD_1$, the first and second fingertip receiving blank side edges 52, 53 may be fixed relative to each other along the partial overlap. Non-limiting examples of how to fix the first and second fingertip receiving blank side edges 52, 53 along the partial overlap include adhesive bonding, stitching, ultrasonic sewing, fastener, and the like. Once fixed to each other, a seam 80, 80a may be created between the first and second fingertip receiving blank side edges 52, 53, whereby the seam 80, 80a extends along the outer surface 14b of the conical wall 14 of the fingertip receiving portion 13 of the ear cleaning apparatus 11. According to this embodiment, the seam 80, 80a may be arranged substantially symmetrically with at least one of the cone axis A-A and/or the grip axis B-B. The seam 80, 80a may extend from the apex 20 to the open end 18 of the conical wall 16.

Referring now to FIGS. 15A and 15B, according to some embodiments the fingertip receiving blank portion 50b may be folded along a fold direction $FD_2$ such that the first fingertip receiving blank side 56 meets the second fingertip receiving blank side edge 57 at a distance that is substantially non-equidistance between the first and second fingertip receiving blank side edges 56, 57. Meeting the first and second fingertip receiving blank side edges 56, 57 may create a partial overlap therein.

Once folded along the fold direction $FD_2$, the first and second fingertip receiving blank side edges 56, 57 may be fixed relative to each other along the partial overlap. Non-limiting examples of how to fix the first and second fingertip receiving blank side edges 56, 57 along the partial overlap include adhesive bonding, stitching, fastener, and the like. Once fixed to each other, a seam 80, 80b may be created between the first and second fingertip receiving blank side edges 56, 57, whereby the seam 80, 80b extends along the outer surface 14b of the conical wall 14 of the fingertip receiving portion 13 of the ear cleaning apparatus 11. According to this embodiment, the seam 80, 80b may be arranged substantially asymmetrically with respect to at least one of the cone axis A-A and/or the grip axis B-B. The seam 80, 80b may extend from the apex 20 to the open end 18 of the conical wall 16. The resulting ear cleaning apparatus 11 may comprise the first fingertip receiving blank side edge 56 forming at least a portion of the lower edge 14c of the conical wall 14. In particular, the resulting ear cleaning apparatus 11 may comprise the first fingertip receiving blank side edge 56 forming at least a portion of the lower edge 14c of the conical wall 14 that extends across opposite sides of the cone axis A-A and the grip axis B-B.

Figure 19:
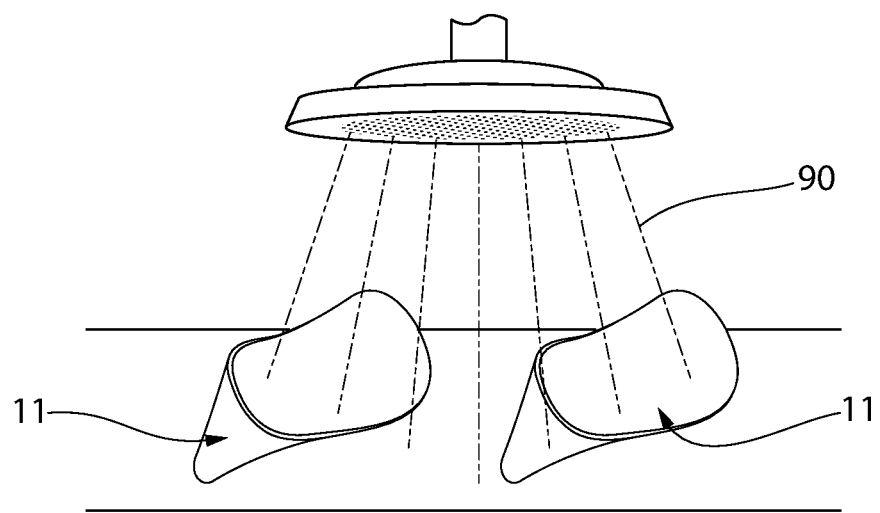
FIG. 19 illustrates a method of treating the fingertip cleaning apparatus of the present invention.

Referring now to FIG. 19, the ear cleaning apparatus 11 of the present invention may be further modified to enhance cleaning performance during use. Specifically, the ear cleaning apparatus 11 may be pre-treated with a cleaning solution 90. The cleaning solution 90 may comprise a hydrophilic component. The cleaning solution 90 may comprise an oleophilic component. The cleaning solution 90 may comprise both the hydrophilic component and the oleophilic component as a surfactant. Non-limiting examples of the surfactant include polyoxyethylene hydrogenated castor oil. The cleaning solution 90 may further comprise one or more of water, propylene glycol, methylparaben, phenoxethol, and/or sodium lactate.

The ear cleaning apparatus 11 may be pre-treated with the cleaning solution such that the outer surface 14b of the conical wall 14 comprises the cleaning solution 90. In other embodiments, other portions of the ear cleaning apparatus 11 may be pre-treated with the cleaning solution 90.

Figure 20:
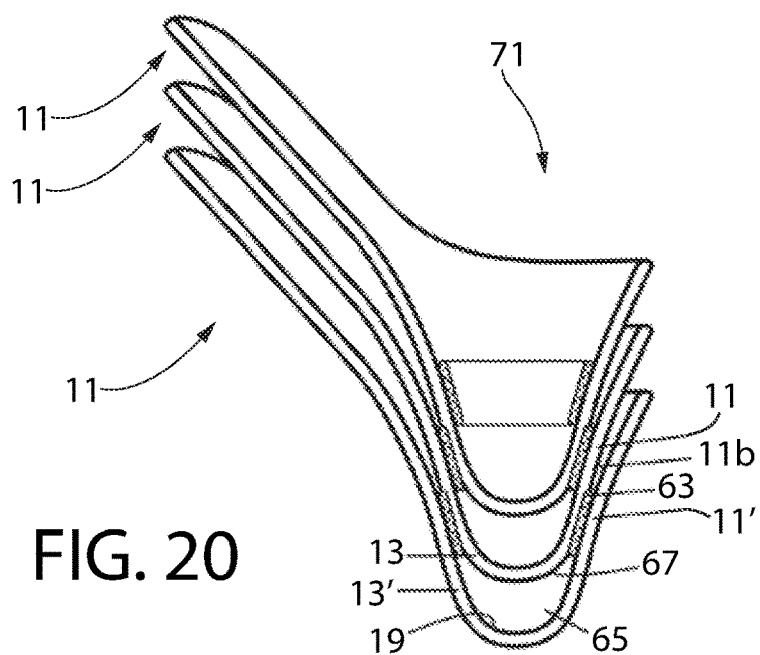
FIG. 20 illustrates a plurality of the fingertip cleaning apparatus of the present invention in a stacked arrangement.
Figure 22:
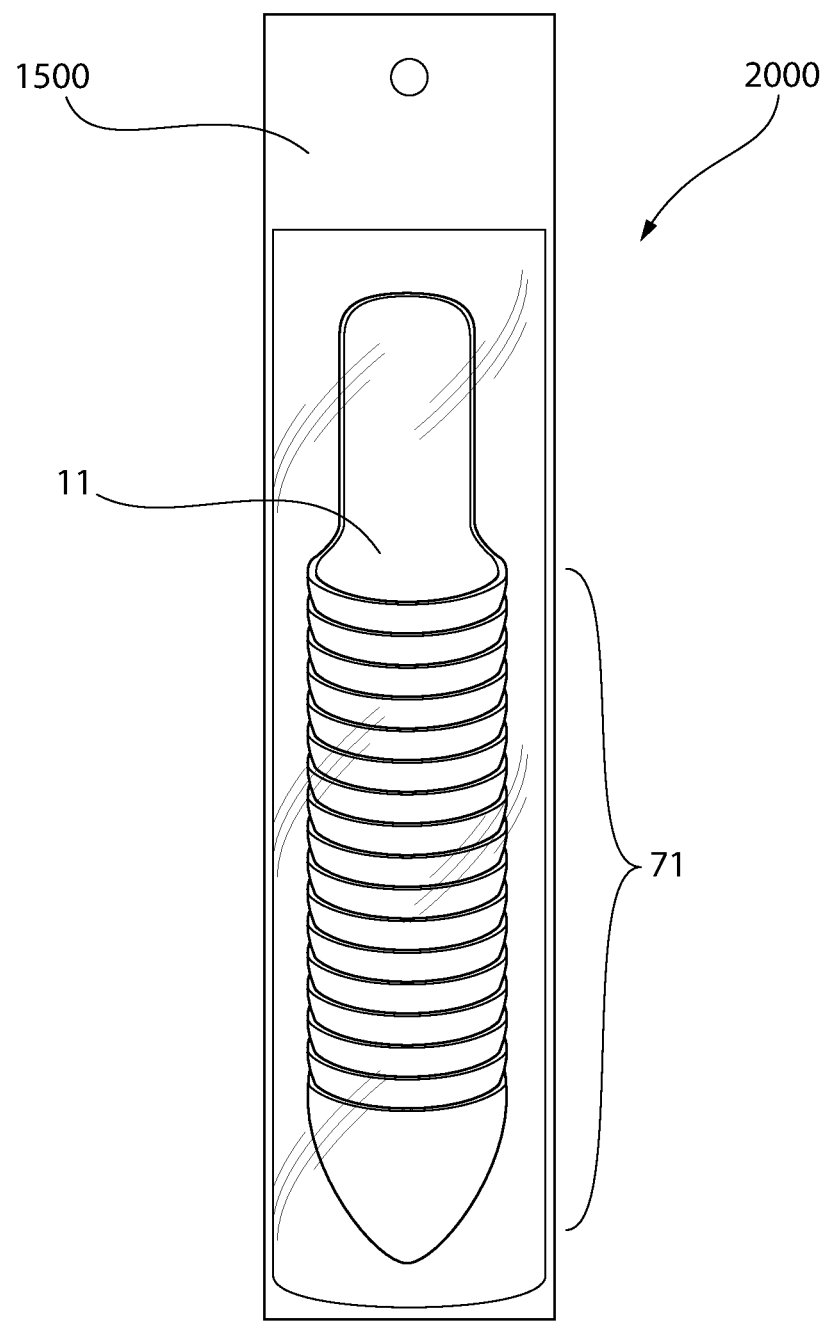
FIG. 22 is a kit comprising a plurality of the fingertip cleaning apparatus of the present invention.

FIGS. 20 and 22 show a plurality of ear cleaning apparatuses 11 placed in a stacked arrangement 71. In this stacked arrangement, the fingertip receiving portion 13 of a first ear cleaning apparatus 11 is nested inside the cavity 16 of the conical wall 14 of the fingertip receiving portion 13' of a second ear cleaning apparatus 11'. The outer surface 11b, specifically the outer surface 14b of the conical wall 14, presses against the inner surface 14a of the conical wall 14 to create an enclosed space 65 between the external tip 67 of the fingertip receiving portion 13 of an ear cleaning apparatus 11 and the closed end 19 of the cavity 16 of the fingertip receiving portion 13 of a second ear cleaning apparatus 11'.

Figures 21A, 21B:
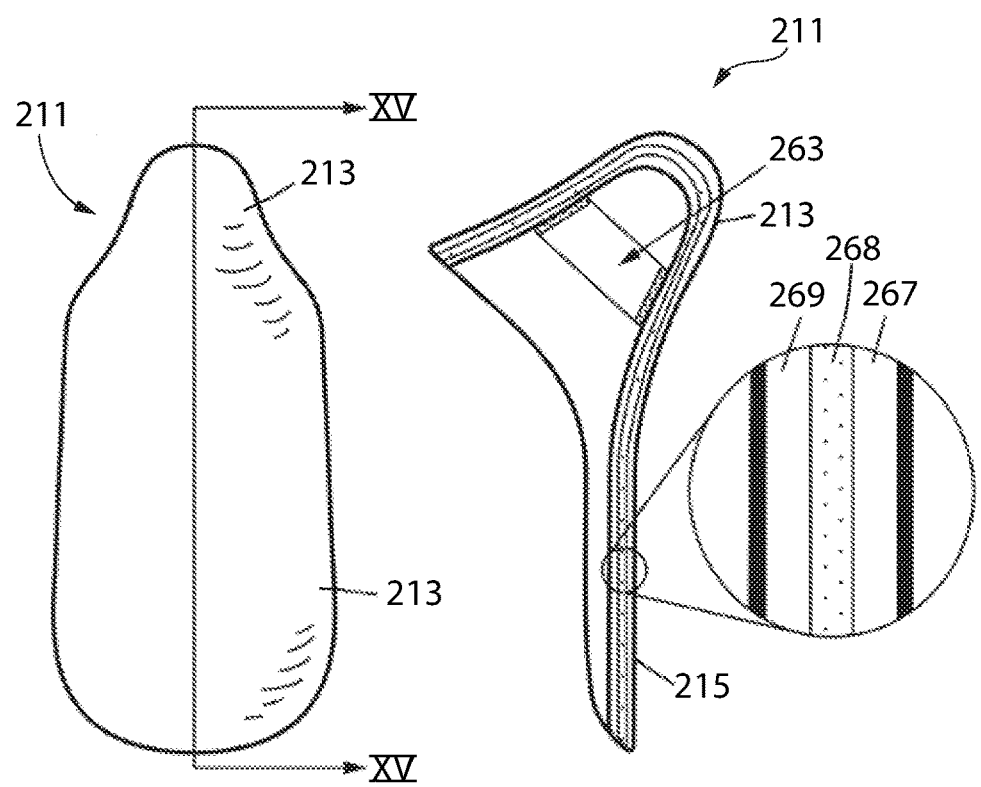

Referring now to FIGS. 20-21B, liquid may be maintained within this enclosed space 65, by sufficient compression against the outer surface 14b of the conical wall 14b of the first fingertip cleaning apparatus 11 and the inner surface 14c of the second fingertip cleaning apparatus 11'. The enclosed space 65 may create a moisture tight enclosure that can prevent substantial loss of liquid that has been pre-applied to the tip 67 of the fingertip cleaning apparatus 11 due to evaporation over an extended period of time. The liquid contained in the enclosed space 65 may be the cleaning composition 90 applied during pre-treatment of the ear cleaning apparatus 11. Thus, in the stacked arrangement 71, the ear cleaning apparatus 11 may each have the external tips 67 pre-moistened with a cleaning solution 90, whereby the adjacent ear cleaning apparatus 11 helps to preserve the pre-moistened state of the nested ear cleaning apparatus 11.

In some embodiments, a barrier band 63 may be included as a lining on the inner surface 14a of the conical wall 14 of the fingertip receiving portion 13. The barrier band 63 of the second ear cleaning apparatus 11' presses against the outer surface 11b of the first ear cleaning apparatus 11—specifically the outer surface 14b of the conical wall 14—to create an enclosed space 65 between the external tip 67 of the fingertip receiving portion 13 of an ear cleaning apparatus 11 and the closed end 19 of the cavity 16 of the fingertip receiving portion 13 of a second ear cleaning apparatus 11'. The barrier band 63 of each ear cleaning apparatus 11 may further help preserve the pre-moistened state of the nested ear cleaning apparatus 11 by further sealing the enclosed space 65 created between adjacent fingertip cleaning apparatus 11, 11'.

Referring now to FIG. 22, the plurality of ear cleaning apparatuses 11 placed in a stacked arrangement 71 may be placed into a packaging 1500, which may or may not form an air-tight seal around the plurality of ear cleaning apparatuses 11. Together, the combination of the plurality of ear cleaning apparatuses 11 contained within the packaging 1500 form a kit 2000, which may be made available for sale to consumers.

Referring now to FIGS. 24-32, additional embodiments of the ear cleaning apparatus of present invention will be provided. The description of the ear cleaning apparatus 11, 211 above generally applies to the following embodiments described below except with regard to the differences specifically noted below. A similar numbering scheme will be used for the ear cleaning apparatus 311, 411, 511, 611, 711, 811, 911, 1111, and 1211 as with the ear cleaning apparatuses 11 and 212 except that the 300-series, 400-series, 500-series, 600-series, 700-series, 800-series, 900-series, 1100-series, and 1200-series of numbers will be used.

Figure 24:
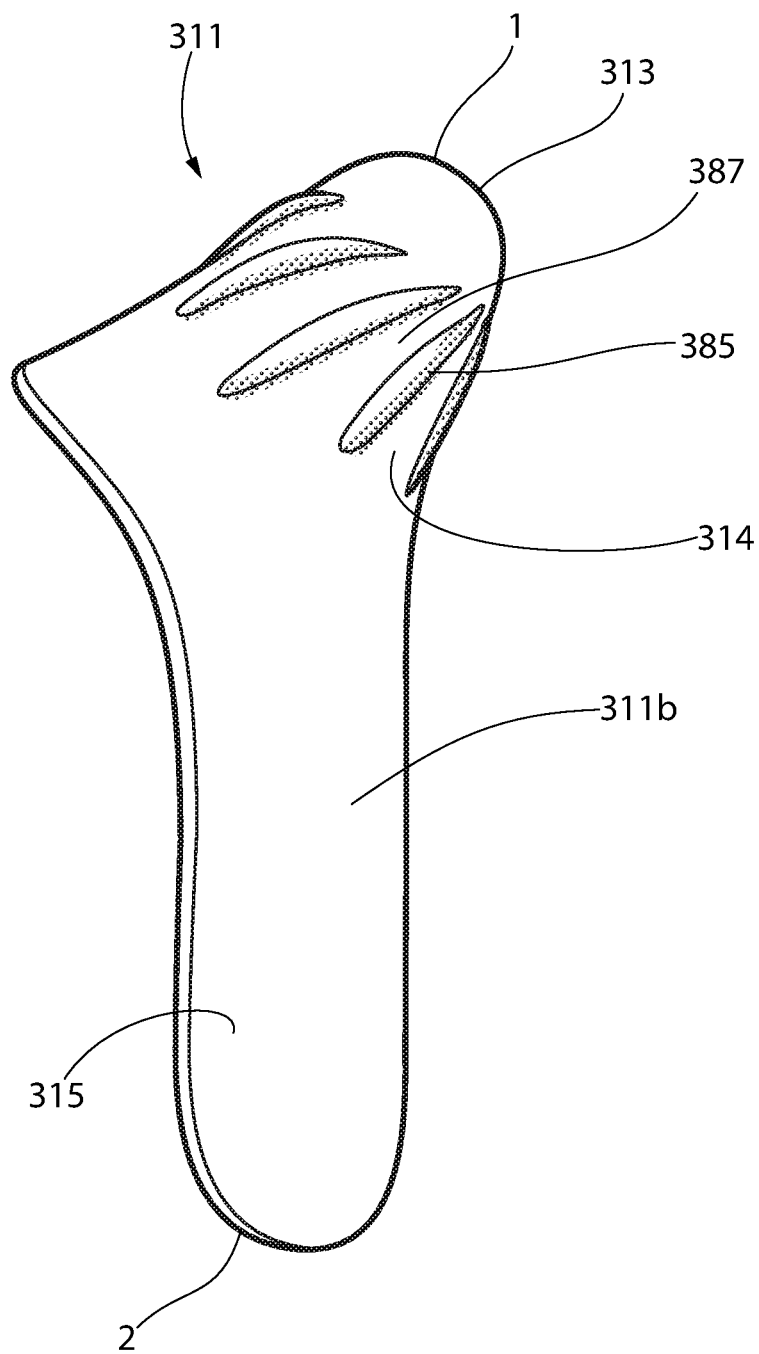
FIG. 24 is a rear view of the fingertip cleaning apparatus according to another embodiment of the present invention.
Figures 25A, 25B:
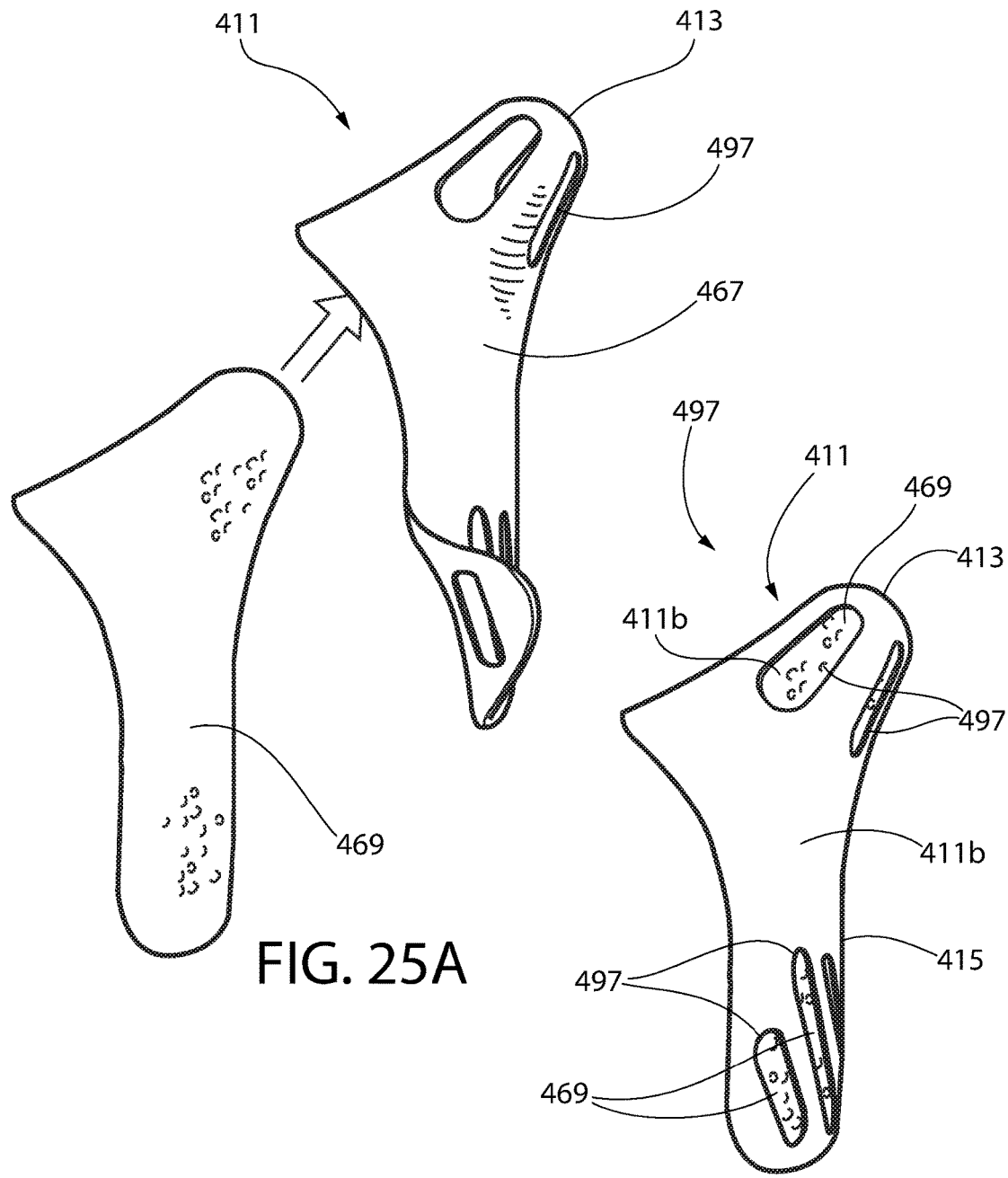
FIG. 25A is an exploded view of the fingertip cleaning apparatus according to another embodiment of the present invention.
FIG. 25B is the fingertip cleaning apparatus of FIG. 25A.

Referring to FIG. 24 in particular, an ear cleaning apparatus 311 according to another embodiment of the present invention may comprise a texture placed on the outer surface of the fingertip receiving portion 313. In multi-layer embodiments, the texture may be formed in just the outer layer, or it may be formed in both the outer layer and any one or more underlying layers. As shown, the texture is a plurality of ridges 385 and valleys 387, both of which extend around the external surface of the fingertip receiving portion 383 so that they are non-parallel to the cone axis formed by the fingertip receiving portion 383.

Referring to FIGS. 13A-B, an ear cleaning apparatus 411 according to another embodiment of the present invention may comprise a multi-layer construction. The overall shape of the fingertip receiving portion 413 and the gripping portion 415 of this ear cleaning apparatus 411 is similar to the ear cleaning apparatus 11 and 211 of FIGS. 1-15B. Both the fingertip receiving portion 413 and the gripping portion 415 include apertures 497 formed in the outer layer 467. Any number of apertures 497 may be included on either of the fingertip receiving portion 413 and the gripping portion 415. The apertures 497 may also have any desired geometric shape, such as the elongate shape shown, or alternatively circular, square, irregular, or any combination of shapes. When the outer layer 467 is coupled to the structural layer 469, portions of the structural layer 469 are exposed through the apertures 497. The exposed portions of the structural layer 469 may be formed as a textured surface. By forming the ear cleaning apparatus 411 in this manner, both the fingertip receiving portion 413 and the gripping portion 415 include multi-purpose cleaning surfaces which have part of the surface formed with the absorbency and softness of the outer layer 467 interspersed with a textured surface formed by the structural layer 469. Stated otherwise, the outer surface 411b of the ear cleaning apparatus may comprise both the outer layer 467 and the inner layer 469.

Figure 26:
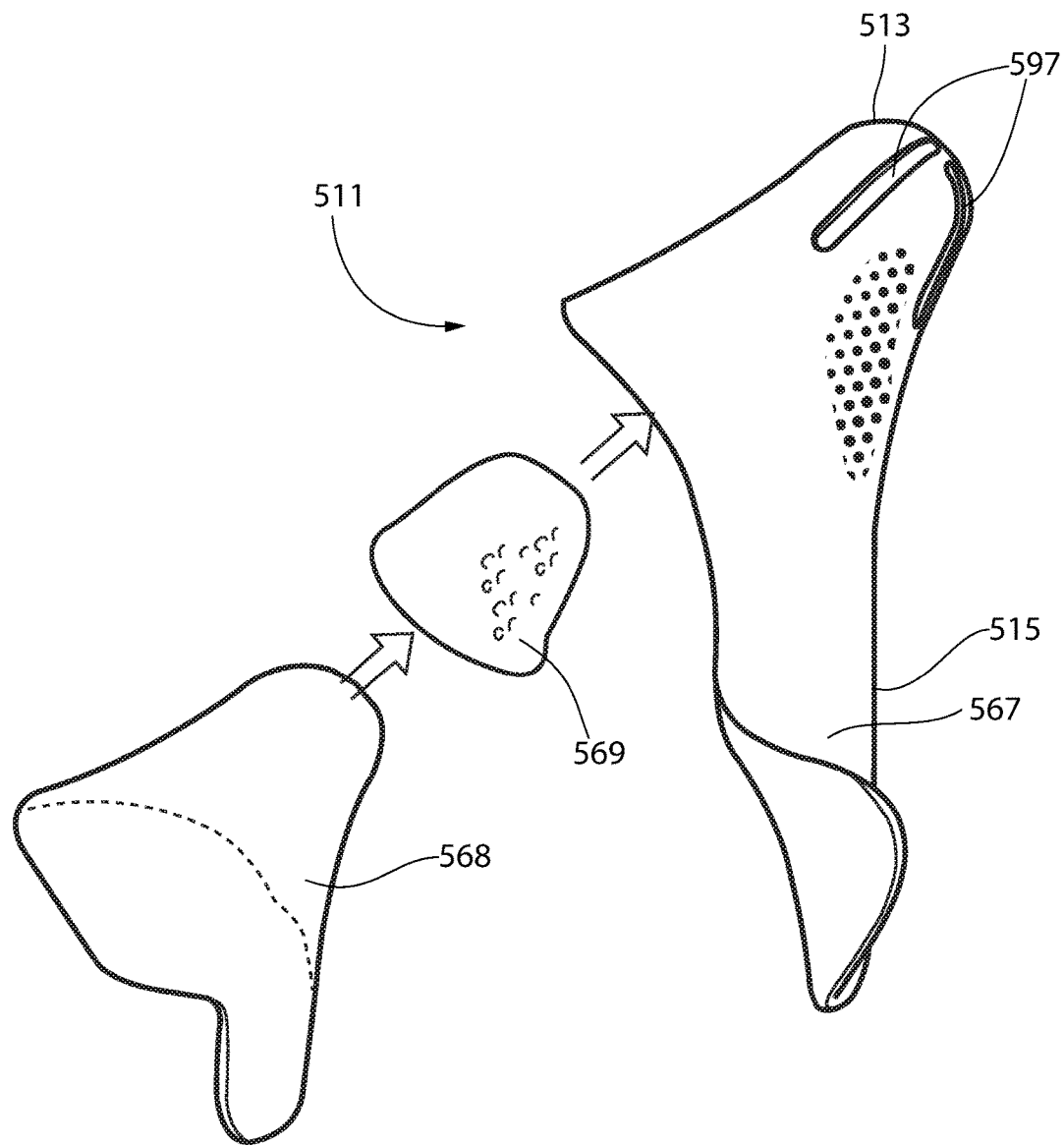
FIG. 26 is an exploded view of the fingertip cleaning apparatus according to another embodiment of the present invention.

Referring now to FIG. 26, an ear cleaning apparatus 511 according to another embodiment of the present invention may comprise a multi-layer construction. The overall shape of the fingertip receiving portion 513 and the gripping portion 515 of this ear cleaning apparatus 511 is similar to the ear cleaning apparatus 11 and 211 of FIGS. 1-15B. In this ear cleaning apparatus 511, the fingertip receiving portion 513 has a multi-layer construction, while the gripping portion 515 has a single-layer construction. An outer layer 567 forms part of both the fingertip receiving portion 513 and the gripping portion 515. As part of the fingertip receiving portion 513, the outer layer 567 includes a plurality of apertures 597. The apertures 597 may have any geometrical shape, whether regular or irregular. The fingertip receiving portion 513 also includes a structural layer 569 and a barrier layer 568, with the structural layer 569 formed as a middle layer between the outer layer 567 and the barrier layer 568. The barrier layer 568 may extend at least partially into the gripping portion 515. The structural layer 569 has a textured surface, part of which is exposed through the apertures 597 formed in the outer layer 567.

Figure 27:
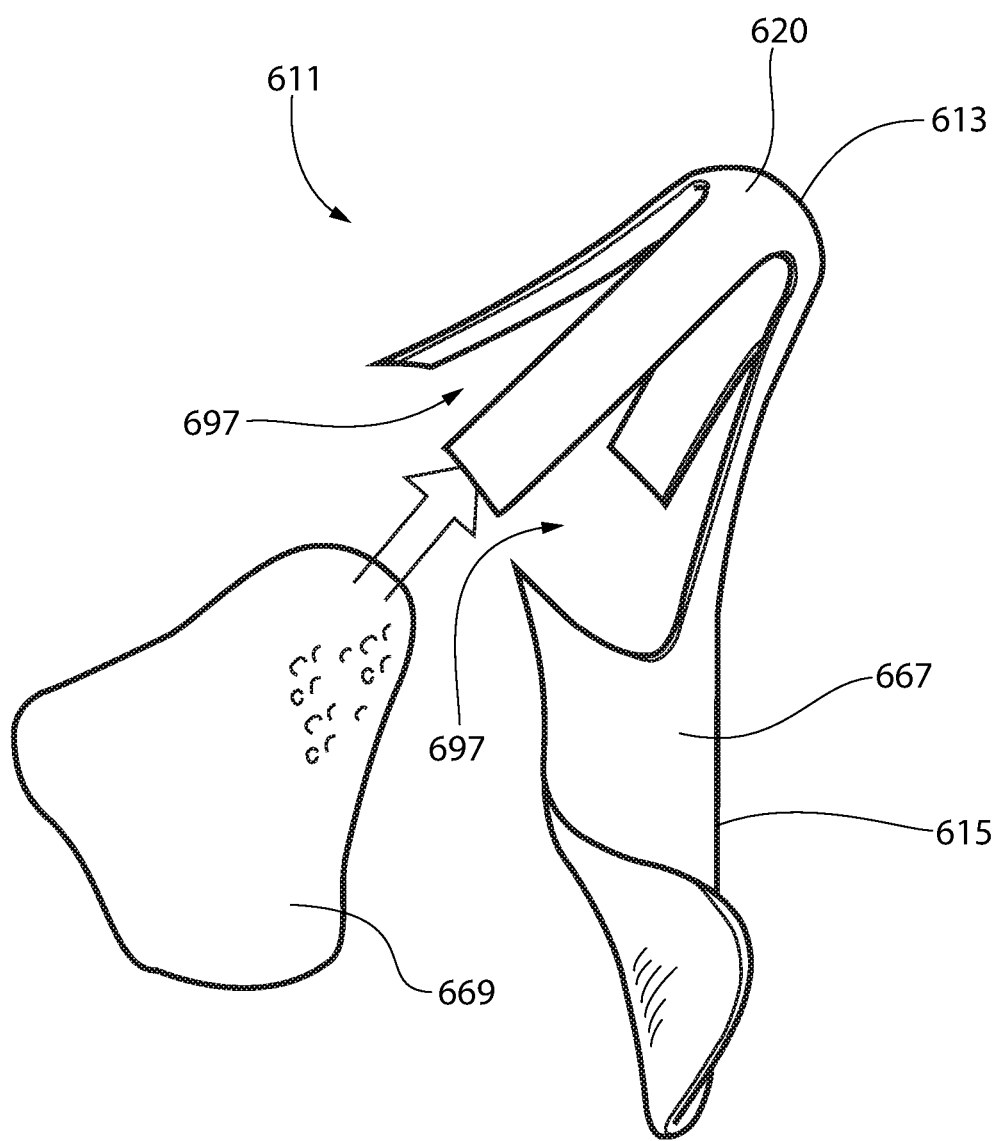
FIG. 27 is an exploded view of the fingertip cleaning apparatus according to another embodiment of the present invention.

Referring now to FIG. 27, an ear cleaning apparatus 611 according to another embodiment of the present invention may comprise a multi-layer construction. The overall shape of the fingertip receiving portion 613 and the gripping portion 615 of this ear cleaning apparatus 611 is similar to the ear cleaning apparatus 11 and 211 of FIGS. 1-15B. In this ear cleaning apparatus 611, the fingertip receiving portion 613 has a multi-layer construction, while the gripping portion 615 has a single-layer construction. An outer layer 677 forms part of both the fingertip receiving portion 613 and the gripping portion 615. As part of the fingertip receiving portion 613, the outer layer 667 includes a plurality of slots 697 extending from an edge of the fingertip receiving portion 613 toward the tip 620. The slots 697 may have any geometrical shape, whether regular or irregular. A structural layer 669 also forms part of the fingertip receiving portion 613. The structural layer 669 has a textured surface, part of which is exposed through the slots 697 formed in the outer layer 667.

Figure 28:
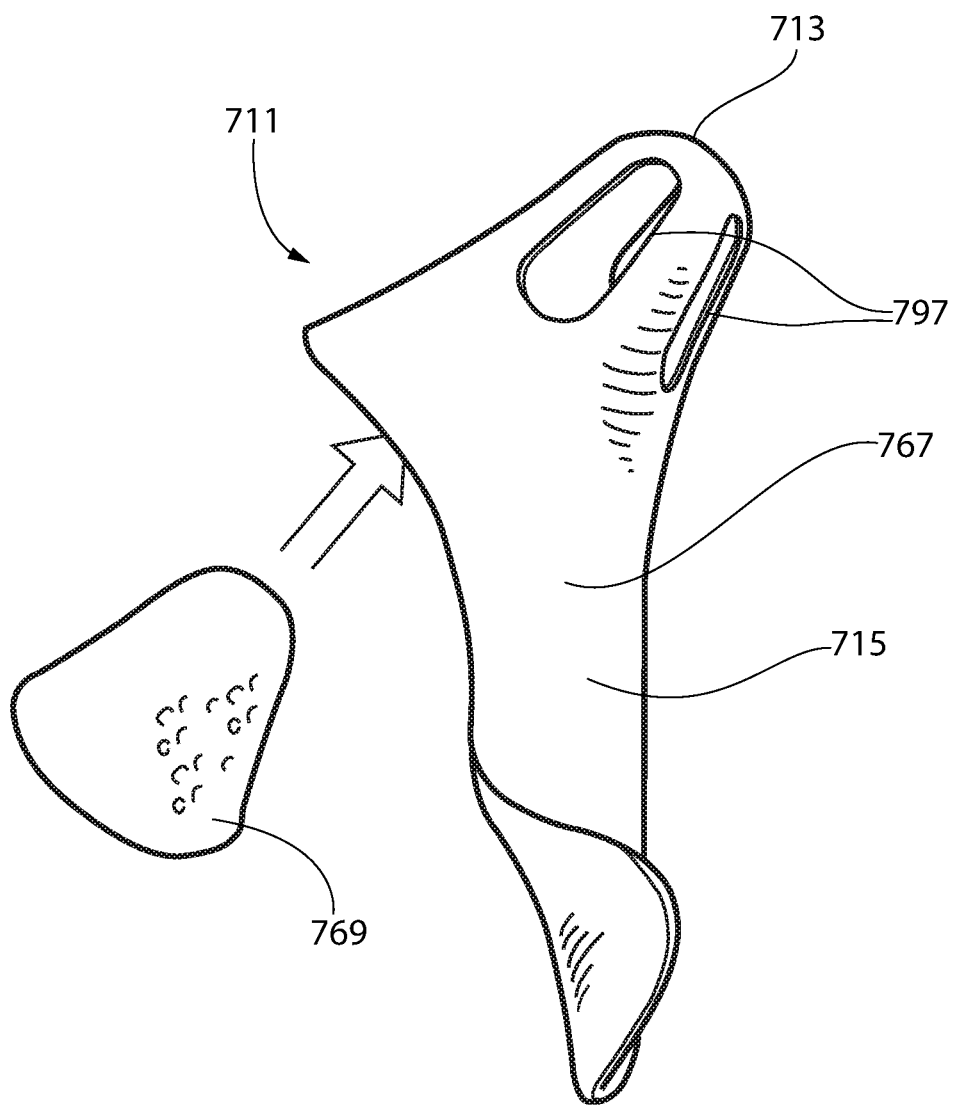
FIG. 28 is an exploded view of the fingertip cleaning apparatus according to another embodiment of the present invention.

Referring now to FIG. 28, an ear cleaning apparatus 711 according to another embodiment of the present invention may comprise a multi-layer construction. The overall shape of the fingertip receiving portion 713 and the gripping portion 715 of this ear cleaning apparatus 711 is similar to the ear cleaning apparatus 11, 211 of FIGS. 1-15B. In this cleaning apparatus 711, the fingertip receiving portion 713 has a multi-layer construction, while the gripping portion 715 has a single-layer construction. An outer layer 767 forms part of both the fingertip receiving portion 713 and the gripping portion 715. As part of the fingertip receiving portion 713, the outer layer 767 includes a plurality of apertures 797. The apertures 797 may have any geometrical shape, whether regular or irregular. A structural layer 769 also forms part of the fingertip receiving portion 713. The structural layer 769 has a textured surface, part of which is exposed through the apertures 797 formed in the outer layer 767.

Figure 29:
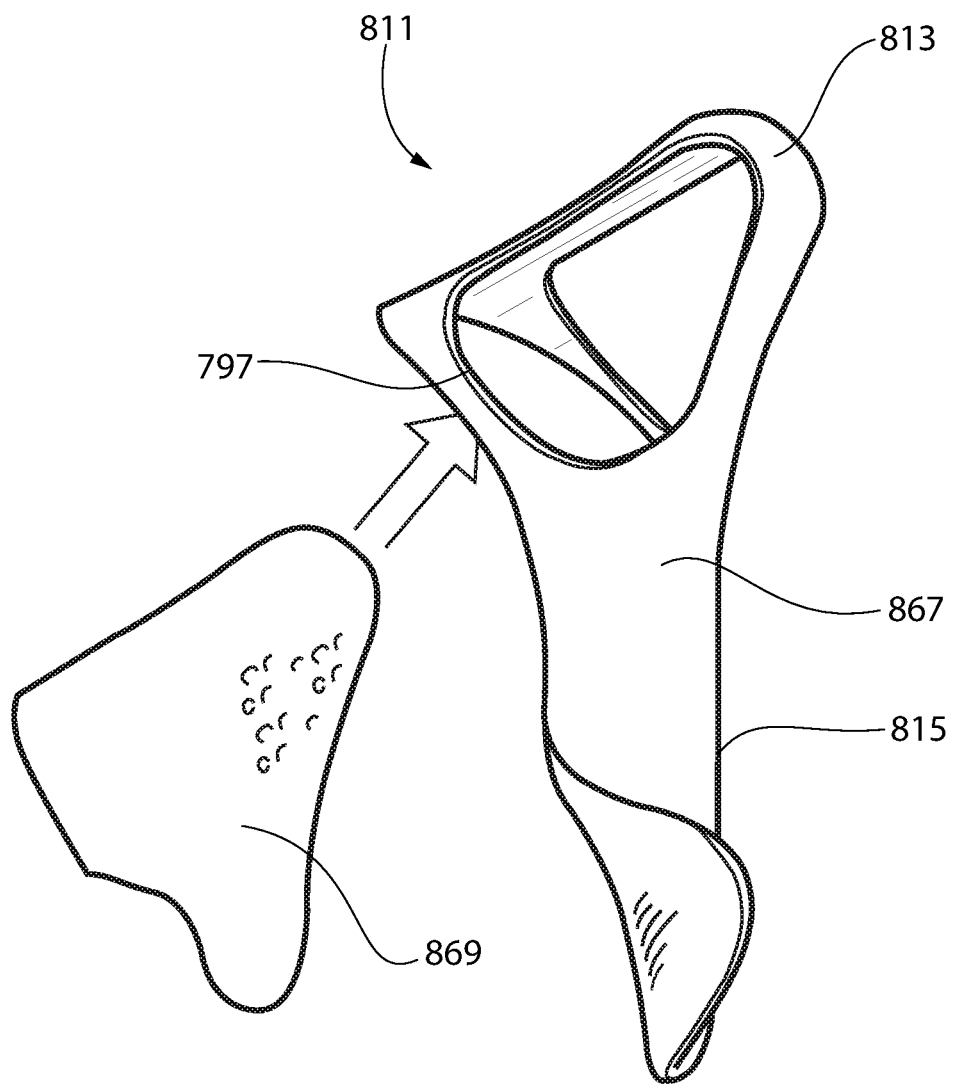
FIG. 29 is an exploded view of the fingertip cleaning apparatus according to another embodiment of the present invention.

Referring now to FIG. 29, an ear cleaning apparatus 811 according to another embodiment of the present invention may comprise a multi-layer construction. The overall shape of the fingertip receiving portion 813 and the gripping portion 815 of this cleaning apparatus 811 is similar to the cleaning apparatus 11, 211 of FIGS. 1-15B. In this cleaning apparatus 811, the fingertip receiving portion 813 has a multi-layer construction, while the gripping portion 815 has a single-layer construction. An outer layer 867 forms part of both the fingertip receiving portion 813 and the gripping portion 815. As part of the fingertip receiving portion 813, the outer layer 867 includes two apertures 897, each being on opposite sides of the fingertip receiving portion 813 from the other. Strips of the outer layer 867 are therefore formed between the two apertures 897. The apertures 897 may have any geometrical shape, whether regular or irregular. A structural layer 869 also forms part of the fingertip receiving portion 813. The structural layer 869 has a textured surface, part of which is exposed through the apertures 897 formed in the outer layer 867.

Figure 30:
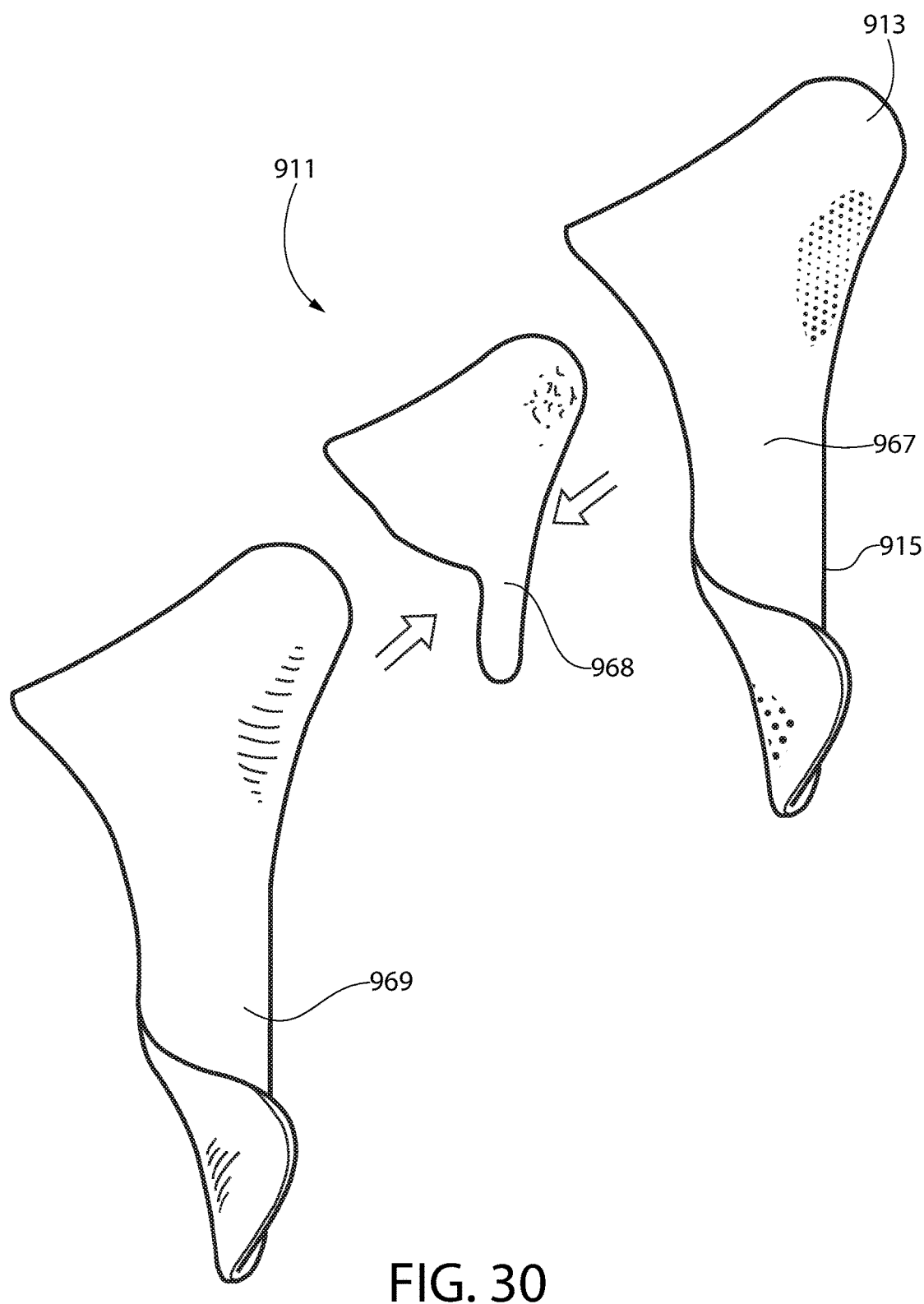
FIG. 30 is an exploded view of the fingertip cleaning apparatus according to another embodiment of the present invention.

Referring now to FIG. 30, an ear cleaning apparatus 911 according to another embodiment of the present invention comprises a multi-layer construction. The overall shape of the fingertip receiving portion 913 and the gripping portion 915 of this cleaning apparatus 911 is similar to the cleaning apparatus 11, 211 of FIGS. 1-15B. In this cleaning apparatus 911, the fingertip receiving portion 913 has a three-layer construction, while the gripping portion 915 has a two-layer construction. The ear cleaning apparatus 911 is formed by an outer layer 967, a barrier layer 968, and a structural layer 969. The outer layer 967 and the structural layer 969 form part of both the fingertip receiving portion 913 and the gripping portion 915, while the barrier layer 968 forms only part of the fingertip receiving portion 913.

Figure 31:
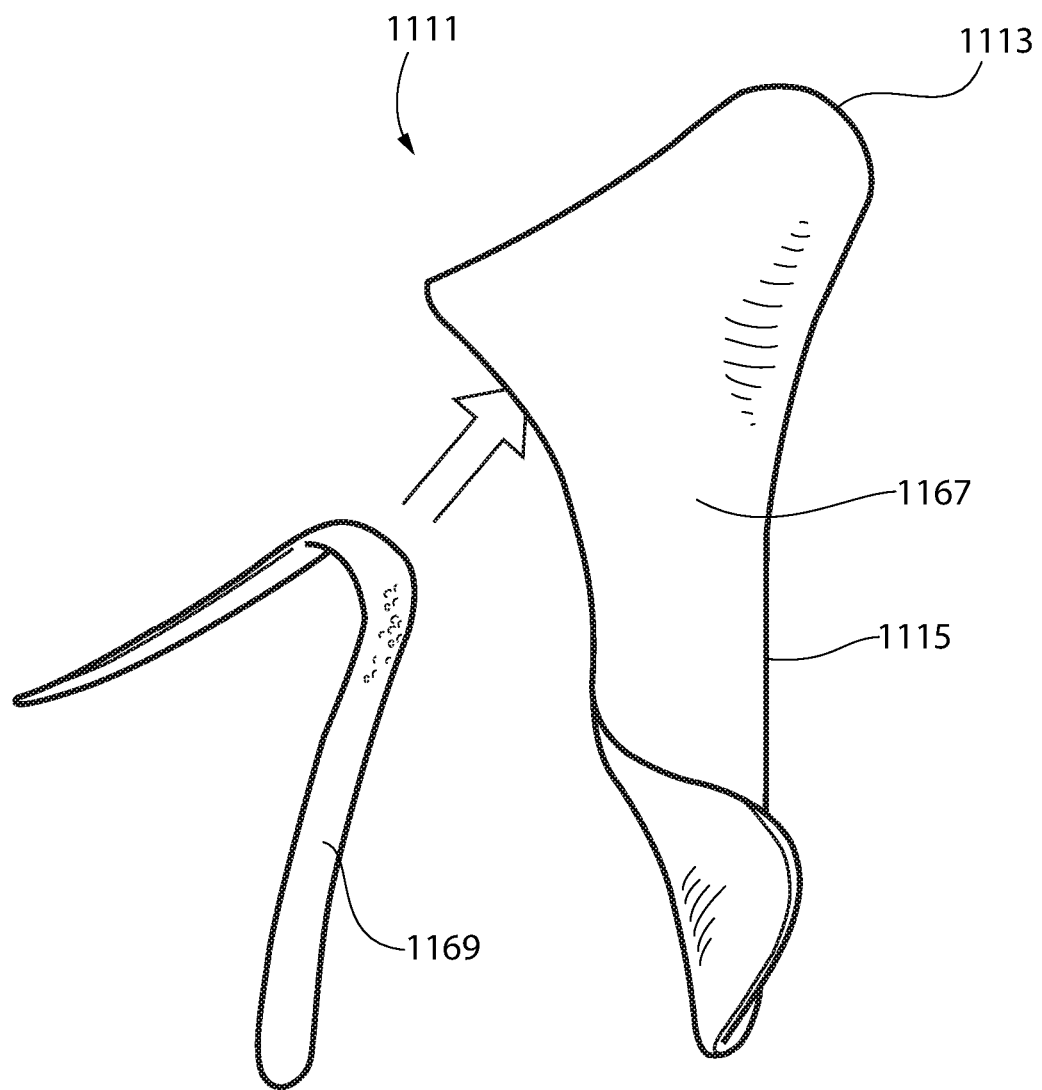
FIG. 31 is an exploded view of the fingertip cleaning apparatus according to another embodiment of the present invention.

Referring now to FIG. 31, an ear cleaning apparatus 1111 according to another embodiment comprises a multi-layer construction. The overall shape of the fingertip receiving portion 1113 and the gripping portion 1115 of this ear cleaning apparatus 1111 is similar to the ear cleaning apparatus 11, 211 of FIGS. 1-15B. In this ear cleaning apparatus 1111, the fingertip receiving portion 1113 has a two-layer construction, while the gripping portion 1115 has a single-layer construction. An outer layer 1167 forms part of both the fingertip receiving portion 1113 and the gripping portion 1115. The fingertip receiving portion 1113 includes a structural layer 1169 formed as a strip of material which extends along two sides and the tip of the fingertip receiving portion 1113. By forming the structural layer 1169 as a strip of material, some of the advantages of having the structural layer 1169 may still be realized, such as providing some structure to the outer layer 1167, while also reducing manufacturing costs by reducing the amount of material needed to form the structural layer 1169.

Figure 32:
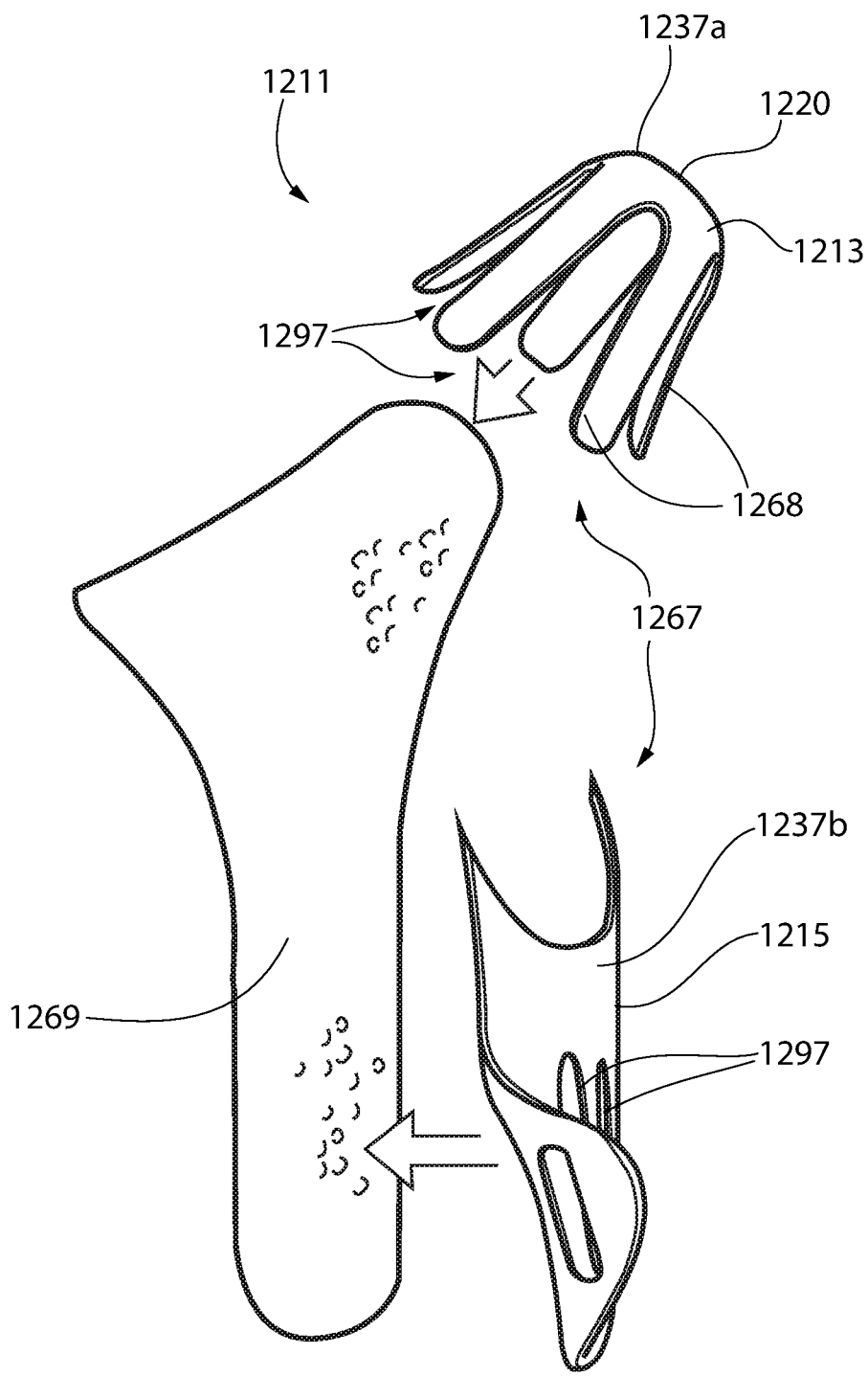
FIG. 32 is an exploded view of the fingertip cleaning apparatus according to another embodiment of the present invention.

Referring now to FIG. 32, an ear cleaning apparatus 1211 according to another embodiment comprises a multi-layer construction. The overall shape of the fingertip receiving portion 1213 and the gripping portion 1215 of this ear cleaning apparatus 1211 is similar to the ear cleaning apparatus 11, 211 of FIGS. 1-15B. In this ear cleaning apparatus 1211, both the fingertip receiving portion 1213 and the gripping portion 1235 have a two-layer construction, each having an outer layer 1267 and a structural layer 1269. The outer layer 1267 is formed in two separate parts, a first part 1237*a* for the fingertip receiving portion 1213 and a second part 1237*b* for the gripping portion 1215. The first part 1237*a* of the outer layer 1267 includes a plurality of fingers extending from the tip 1220 of the fingertip receiving portion 1213, with a space 1297 being formed between adjacent fingers. The first part 1237*a* may include any number of fingers and spaces 1297. The second part 1237*b* of the outer layer 1267 includes apertures 1297. The second part 1237*a* may include any number of apertures 1297, and the apertures 1297 may have any desired geometric shape or combination of shapes. With the first and second parts 1237*a*, 1237*b* of the outer layer 167 coupled to the structural layer 1269, portions of the structural layer 1269 are exposed through the spaces 1297 between the fingers of the first part 1237*a* and through the apertures 1297 of the second part 1237*b*. The exposed portions of the structural layer 1269 may be formed as a textured surface. By forming the ear cleaning apparatus 1211 in this manner, both the fingertip receiving portion 1213 and the gripping portion 1215 include multi-purpose cleaning surfaces which have part of the surface formed with the absorbency and softness of the outer layer 1267 interspersed with a textured surface formed by the structural layer 1269.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly.

What is claimed is:

1. A fingertip cleaning apparatus comprising:
a single sheet of fibrous material in a three-dimensional configuration, the three-dimensional configuration comprising:
a fingertip receiving portion comprising a conical wall extending from a proximal end to a distal end along a cone axis, a cavity having a top end that is closed at the distal end of the conical wall, and an opening into the cavity at the proximal end of the conical wall that is defined, at least in part, by an exposed portion of a lower edge of the conical wall, the conical wall forming a cone angle with the cone axis, the conical wall having a first length measured along the cone axis from the proximal end of the conical wall to the distal end of the conical wall; and
a gripping portion comprising a flap that extends from the proximal end of the conical wall of the fingertip receiving portion along a grip axis that forms a grip angle with the cone axis, the flap having a lower edge and a second length measured along the grip axis from the proximal end of the conical wall to the lower edge of the flap;
wherein the grip angle is equal to or greater than the cone angle;
wherein the second length is greater than the first length, the second length being between 30 mm and 50 mm;
wherein an outer surface of the gripping portion is continuous with an outer surface of the fingertip receiving portion such that the three-dimensional configuration comprises a smooth and uninterrupted outer surface;
wherein the fibrous material is absorbent and pre-treated with a cleaning solution; and
wherein the exposed portion of the lower edge of the conical wall is oblique to the grip axis.

2. The fingertip cleaning apparatus according claim 1 wherein a sum of the first and second lengths is between 55 mm and 70 mm.

3. The fingertip cleaning apparatus according to claim 1 wherein the cleaning solution comprises phenoxethol.

4. The fingertip cleaning apparatus according to claim 1 wherein the flap comprises a first side edge extending from the proximal end of the conical wall to the lower edge of the flap and a second side edge extending from the proximal end of the conical wall to the lower edge of the flap, and wherein the exposed portion of the lower edge of the conical wall is oblique to the first and second side edges of the flap.

5. The fingertip cleaning apparatus according to claim 1 wherein the flap has a convex outer surface, a concave inner surface and a curved transverse cross-sectional profile taken along the grip axis.

6. The fingertip cleaning apparatus according to claim 1 wherein the conical wall has an outer surface and the flap has an outer surface, the flap extending from the conical wall such that the outer surface of the flap and the outer surface of the conical wall collectively define a smooth uninterrupted surface.

7. The fingertip cleaning apparatus according to claim 1 wherein the fibrous material is non-woven.

8. The fingertip cleaning apparatus according to claim 1 further comprising:
the flap comprises a first side edge, a second side edge opposite the first side edge, and the lower edge extending between the first and second side edges; and
the first side edge, the second side edge, and the lower edge of the flap, and the lower edge of the conical wall collectively defining a continuous, smooth, and uninterrupted edge of the fingertip cleaning apparatus.

9. The fingertip cleaning apparatus according to claim 1 wherein the flap has a first maximum width and the cavity has a second maximum width that is less than the first maximum width.

10. The fingertip cleaning apparatus according to claim 1 wherein an outer surface of the flap and an outer surface of the conical wall extend along an axis, and wherein the exposed portion of the lower edge of the conical wall lies in a plane that is oblique to the axis.

11. The fingertip cleaning apparatus according to claim 1 wherein the flap comprises first and second side edges that are oblique to the exposed portion of the lower edge of the conical wall.

12. The fingertip cleaning apparatus according to claim 11 wherein the first and second side edges of the flap intersect the exposed portion of the lower edge of the conical wall at an obtuse angle.

13. A package of fingertip cleaning apparatuses comprising:
a package;
a plurality of fingertip cleaning apparatuses, each of the fingertip cleaning apparatuses comprising:
a fingertip receiving portion including a conical wall extending from a proximal end to a distal end, the conical wall tapering continuously from the proximal end to a rounded apex at the distal end, the conical wall defining a cavity having an opening at the proximal end that is defined, at least in part, by an exposed portion of a lower edge of the conical wall; and
a gripping portion comprising a flap that extends from the proximal end of the conical wall of the fingertip receiving portion;
the plurality of fingertip cleaning apparatuses disposed within the package and arranged in a stack so that the fingertip receiving portions of each of the fingertip cleaning apparatuses nests within the cavity of an adjacent one of the plurality of wherein each of the fingertip cleaning apparatuses comprises a single sheet of fibrous material in a three-dimensional configuration, wherein the fibrous material is pre-treated with a cleaning solution, and wherein an outer surface of the gripping portion is continuous with an outer surface of the fingertip receiving portion such that the three-dimensional configuration comprises a smooth and uninterrupted outer surface.

14. The package of fingertip cleaning apparatuses according to claim 13 wherein the conical wall comprises a cone axis, the conical wall having a first length measured along the cone axis from the proximal end of the conical wall to the distal end of the conical wall, and wherein the flap extends from the proximal end of the conical wall to a distal edge along a grip axis, the flap having a second length measured along the grip axis from the proximal end of the conical wall to the distal edge of the flap, the second length being greater than the first length.

15. The package of fingertip cleaning apparatuses according to claim 13 further comprising a single sheet of fabric having a three-dimensional structure that comprises the fingertip receiving portion and the gripping portion of each of the fingertip cleaning apparatuses, and wherein the three-dimensional structure is maintained in a three-dimensional configuration in an unused state in which the cavity is empty.

16. The fingertip cleaning apparatus according to claim 13 wherein the flap comprises first and second side edges that extend from the proximal end of the conical wall and are oblique to the exposed portion of the lower edge of the conical wall.

17. A fingertip cleaning apparatus comprising:
a single sheet of fibrous material in a three-dimensional configuration, the three-dimensional configuration comprising:
a fingertip receiving portion comprising a conical wall having a rounded apex at a distal end of the conical wall, a cavity having a top end that is closed by the rounded apex, and an opening into the cavity defined, at least in part, by an exposed portion of a lower edge of the conical wall; and
a gripping portion comprising a flap that extends from a proximal end of the conical wall of the fingertip receiving portion along a grip axis that forms a grip angle with the cone axis;
wherein the three-dimensional configuration is maintained in an unused state in which the cavity is empty;
wherein an outer surface of the gripping portion is continuous with an outer surface of the fingertip receiving portion such that the three-dimensional configuration comprises an uninterrupted outer surface;
wherein the fibrous material forms a texture on a portion of the outer surface of the three-dimensional configuration; and
wherein the fibrous material is absorbent and pre-treated with a cleaning solution comprising phenoxethol.

18. The fingertip cleaning apparatus according to claim 17 wherein the conical wall extends along a cone axis and has a first length measured along the cone axis from the proximal end of the conical wall to the distal end of the conical wall, and wherein the flap extends along a grip axis and has a second length measured along the grip axis from the proximal end of the conical wall to a distal end of the flap, the second length being greater than the first length.

19. The fingertip cleaning apparatus according to claim 17 wherein the flap extends along a grip axis, and wherein the exposed portion of the lower edge of the conical wall lies in a plane that is oblique to the grip axis.

20. The fingertip cleaning apparatus according to claim 17 wherein the flap comprises first and second side edges that intersect the exposed portion of the lower edge of the conical wall at an obtuse angle.

* * * * *